United States Patent
Old et al.

(10) Patent No.: US 9,926,262 B2
(45) Date of Patent: Mar. 27, 2018

(54) EP4 AGONISTS AS THERAPEUTIC COMPOUNDS

(71) Applicant: ALLERGAN, INC., Irvine, CA (US)

(72) Inventors: David W. Old, Irvine, CA (US); Christopher D. Hein, Irvine, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 15/316,786

(22) PCT Filed: Jun. 5, 2015

(86) PCT No.: PCT/US2015/034566
§ 371 (c)(1),
(2) Date: Dec. 6, 2016

(87) PCT Pub. No.: WO2015/188152
PCT Pub. Date: Dec. 10, 2015

(65) Prior Publication Data
US 2017/0183293 A1    Jun. 29, 2017

Related U.S. Application Data

(60) Provisional application No. 62/009,028, filed on Jun. 6, 2014.

(51) Int. Cl.
*C07C 235/40*      (2006.01)
*C07C 233/63*      (2006.01)

(52) U.S. Cl.
CPC .......... *C07C 235/40* (2013.01); *C07C 233/63* (2013.01); *C07C 2101/08* (2013.01); *C07C 2101/10* (2013.01); *C07C 2101/14* (2013.01); *C07C 2101/16* (2013.01); *C07C 2101/18* (2013.01); *C07C 2102/42* (2013.01)

(58) Field of Classification Search
None
See application file for complete search history.

(56) References Cited

U.S. PATENT DOCUMENTS

| | | | |
|---|---|---|---|
| 4,166,452 A | 9/1979 | Generales, Jr. |
| 4,256,108 A | 3/1981 | Theeuwes |
| 4,265,874 A | 5/1981 | Bonsen et al. |
| 4,540,690 A | 9/1985 | Szmuszkovicz |
| 5,420,343 A | 5/1995 | Koszyk et al. |
| 6,410,781 B1 | 6/2002 | Konradi et al. |
| 6,552,067 B2 | 4/2003 | Cameron |
| 6,586,468 B1 | 7/2003 | Maruyama |
| 7,427,685 B2 | 9/2008 | Donde et al. |

FOREIGN PATENT DOCUMENTS

| | | |
|---|---|---|
| WO | 02102389 | 12/2002 |
| WO | 2007130890 | 11/2007 |
| WO | 2011053870 | 5/2011 |
| WO | 2013004291 | 1/2013 |

OTHER PUBLICATIONS

Ito, Nobuyuki. Cancer Science 94(1), (2003) 3-8.*
Berge, Stephen M., Pharmaceutical Salts, Journal of Pharmaceutical Sciences, Jan. 1977, 1-19, 66 (1), US.
Database Registry, Chemical Abstracts Service, Database Accession No. 1575419-94-1, Mar. 28, 2014, XP002744513.
Datebase Registry, Chemical Abstracts Service, Database Accession No. 1572391-58-2, Mar. 24, 2014, XP002744512.
Kenji Kabashima et al, The Prostaglandin Receptor EP4 Suppresses Colitis, Muscosal Damage and CD4 Cell Activation in the Gut, journal of Clinical Investigation, 2002, 883-893, 109(7).
International Search Report & Written Opinion dated Sep. 25, 2015 for PCT/US15/34566 filed Jun. 5, 2015 in the name of Allergan, Inc.
Remington's Pharmaceutical Sciences, 16th Edition, 10 Pages, 1980.
Database Registry, Chemical Abstracts Service, Database Accession No. 1569570-27-9, Mar. 18, 2014.
Database Registry, Chemical Abstracts Service, Database Accession No. 1574233-61-6, Mar. 26, 2014.

* cited by examiner

*Primary Examiner* — Samantha L Shterengarts
(74) *Attorney, Agent, or Firm* — Jonathan Bass

(57) ABSTRACT

Described herein are compounds that are $EP_4$ agonists and antagonists which are useful for treating a variety of pathological conditions associated with activity of $EP_4$ receptors.

12 Claims, No Drawings

EP4 AGONISTS AS THERAPEUTIC COMPOUNDS

CROSS REFERENCE TO RELATED APPLICATIONS

This application is a national stage application under 371 U.S.C. § 371 of PCT Application PCT/US2015/034566 filed Jun. 5, 2015, which claims the benefit of U.S. provisional application 62/009,028 entitled "Novel EP$_4$ Agonists As Therapeutic Compounds" filed on Jun. 6, 2014 which are incorporated herein by reference in their entireties and serve as the basis of a priority and/or benefit claim for the present application.

FIELD

The present invention relates to compounds and methods for treating disorders and specifically to agonists and antagonists for EP$_4$ receptors.

BACKGROUND

The prostanoid EP$_4$ receptor is a G protein-coupled receptor that mediates the actions of prostaglandin E$_2$ (PGE$_2$) and is characterized by the longest intracellular C terminus loop when compared to other prostanoid receptors. The EP4 receptor is one of four receptor subtypes of prostaglandin E2 receptors. In general, EP$_4$ receptors couple to G proteins and mediate elevations in cyclic-adenosine monophsophate ("cAMP") concentration, although they do participate in other pathways as well. Expression of EP$_4$ receptors is controlled by various physiological and pathophysiological processes as these receptors participate in ovulation and fertilization, induce bone formation, T cell factor signaling, protect against inflammatory bowel disease, facilitate Langerhans cell migration and maturation and mediate joint inflammation in a model of collagen-induced arthritis, among others.

U.S. Pat. No. 6,552,067, expressly incorporated herein by reference, teaches the use of prostaglandin EP$_4$ selective agonists for the treatment of methods of treating conditions which present with low bone mass, particularly osteoporosis, frailty, an osteoporotic fracture, a bone defect, childhood idiopathic bone loss, alveolar bone loss, mandibular bone loss, bone fracture, osteotomy, bone loss associated with periodontitis, or prosthetic ingrowth in a mammal.

U.S. Pat. No. 6,586,468, expressly incorporated herein by reference, teaches that prostaglandin EP$_4$ agonists may be useful for the prophylaxis and/or treatment of autoimmune disorders such as amyotrophic lateral sclerosis, multiple sclerosis, Sjoegren's syndrome, arthritis, rheumatoid arthritis, systemic lupus erythematosus, post-transplantation graft rejection, asthma, abnormal bone formation, neurocyte death, pulmopathy, hepatopathy, acute hepatitis, nephritis, renal insufficiency, hypertension, myocardial ischemia, systemic inflammatory syndrome, pain induced by ambustion, sepsis, hemophagocytosis syndrome, macrophage activation syndrome, Still's diseases, Kawasaki diseases, burns, systemic granuloma, ulcerative colitis, Crohn's diseases, hypercytokinemia at dialysis and multiple organ failure and shock.

Inflammatory bowel disease constitutes a group of diseases characterized by inflammation of the large and small intestines and manifests symptoms such as diarrhea, pain, and weight loss. Kabashima and colleagues taught that "EP$_4$ works to keep mucosal integrity, to suppress the innate immunity, and to down regulate the proliferation and activation of CD4+ T cells. These findings have not only elucidated the mechanisms of IBD by NSAIDs, but also indicated the therapeutic potential of EP$_4$-selective agonists in prevention and treatment of IBD." (Kabashima, et. al., The Journal of Clinical Investigation, April 2002, Vol. 9, 883-893).

Various other diseases are mediated by the EP$_4$ receptor such as esophageal ulcers, alcohol gastropathy, duodenal ulcers, non-steroidal anti-inflammatory drug-induced gastroenteropathy and intestinal ischemia. New methods for treating or preventing such diseases are desired.

SUMMARY

The present invention is directed in part to EP$_4$ agonists and antagonists and their use in treating a variety of pathological conditions associated with activity of the EP$_4$ receptors.

In one embodiment of the invention, there are provided compounds having the structure:

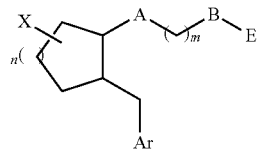

or a pharmaceutically acceptable salt or diastereomer or enantiomer thereof, wherein:

n=0, 1, 2, 3 or 4 m=0 or 1

X is zero (meaning completely absent), or one or two substituents on the cycloalkane or cycloalkene ring, said substituents chosen from the group consisting of H, lower alkyl (e.g., $C_1$-$C_6$), hydroxyalkyl, aryl, halogen, cycloalkene, $CF_3$, C(O)R, $COCF_3$, $SO_2N(R)_2$, $SO_2NH_2$, $NO_2$, and CN;

A is selected form the group consisting of CH=CH, $CH_2CH_2$, C(O)NH, $C(O)NCH_3$, NHC(O), $CH_2O$, $CH_2N(H)$, $CH_2S$, $OCH_2$, $N(H)CH_2$ and $SCH_2$;

B is selected from the group consisting of arylene and heteroarylene, $CH_2$, $CH_2CH_2$, $CH_2CH_2CH_2$, $OCH_2$, $OCH_2CH_2$, and $CH_2OCH_2$;

E is selected from the group consisting of $CO_2R_2$, $CH_2OR_2$, $CONR_2R_3$ or tetrazol-5-yl;

Ar is selected from the groups consisting of unsubstituted or mono-, di-, or tri-substituted aryl and heteroaryl, said substituents chosen from the group consisting of lower alkyl, hydroxyalkyl, aryl, halogen, $OR_3$, $CF_3$, C(O)R, $COCF_3$, $SO_2N(R)_2$, $SO_2NH_2$, $NO_2$, and CN;

R is $C_1$-$C_6$ alkyl;

$R_2$ is selected from the group consisting of H, hydroxyalkyl, $C_1$-$C_6$ alkyl, phenyl or biphenyl;

$R_3$ is selected from the group consisting of H, C(O)$R_5$, $SO_2R_5$, $C_1$-$C_6$ alkyl; and $R_5$ is $C_1$-$C_6$ alkyl, haloalkyl including trifluoromethyl, aryl or heteroaryl.

Another embodiment of the invention includes compounds having the following structure:

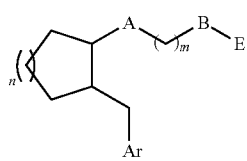

or a pharmaceutically acceptable salt or diastereomer or enantiomers thereof, wherein:
  n=0, 1, 2, 3, or 4;
  m=0 or 1;
  A is selected form the group consisting of CH=CH, $CH_2CH_2$, C(O)NH, $C(O)NCH_3$ NHC(O), $CH_2O$, $CH_2N(H)$, $CH_2S$, $OCH_2$, $N(H)CH_2$ and $SCH_2$;
  B is selected from the group consisting of arylene, heteroarylene, $CH_2$, $CH_2CH_2$, $CH_2CH_2CH_2$, $OCH_2$, $OCH_2CH_2$, and $CH_2OCH_2$;
  E is selected from the group consisting of $CO_2R_2$, $CH_2OR_2$, $CONR_2R_3$ or tetrazol-5-yl;
  Ar is selected from the groups consisting of unsubstituted or mono-, di-, or tri-substituted aryl and heteroaryl, said substituents chosen from the group consisting of lower alkyl, hydroxyalkyl, aryl, halogen, $OR_3$, $CF_3$, C(O)R, $COCF_3$, $SO_2N(R)_2$, $SO_2NH_2$, $NO_2$, and CN;
  R is $C_1$-$C_6$ alkyl;
  $R_2$ is selected from the group consisting of H, hydroxyalkyl, $C_1$-$C_6$ alkyl, phenyl or biphenyl; and
  $R_3$ is selected from the group consisting of H, $C(O)R_5$, $SO_2R_5$, $C_1$-$C_6$ alkyl.

Another embodiment of the invention includes compounds having the following structure:

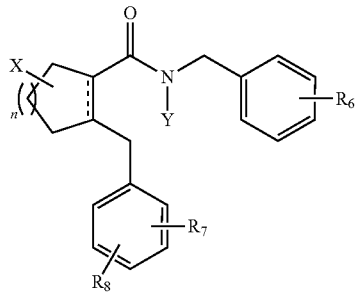

or a pharmaceutically acceptable salt or diastereomer or enantiomer thereof, wherein:
  the dashed line is a single or a double bond;
  Y is H or $CH_3$;
  X is zero (meaning completely absent), one or two substituents on the cycloalkane or cycloalkene ring, said substituents chosen from the group consisting of H, $C_1$-$C_6$ alkyl, hydroxyalkyl, aryl, halogen, cycloalkene, OR, $CF_3$, C(O)R, $COCF_3$, $SO_2N(R)_2$, $SO_2NH_2$, $NO_2$, and CN;
  n is selected from the group consisting of 0, 1, 2, 3, or 4;
  R is $C_1$-$C_6$ alkyl;
  $R_2$ is selected from the group consisting of H, hydroxyalkyl, $C_1$-$C_6$ alkyl, phenyl or biphenyl;
  $R_3$ is selected form the group consisting of H, $C(O)R_5$, $SO_2R_5$, $C_1$-$C_6$ alkyl;
  $R_5$ is $C_1$-$C_6$ alkyl, haloalkyl including trifluoromethyl, aryl or heteroaryl;
  $R_6$ is $CO_2H$, $CH_3$, $CO_2R_2$, $CH_2OR_2$, $CONR_2R_3$ or tetrazol-5-yl;
  $R_7$ is selected from the group consisting of H, $CF_3$, $OCH_3$; and
  $R_8$ is selected form the group consisting of H and $OCH_3$.

Another embodiment of the invention includes compounds having the following structure:

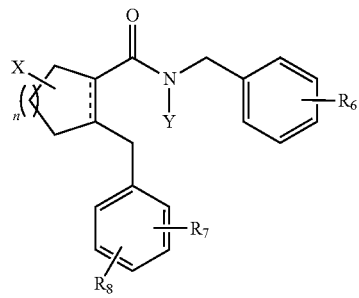

or a pharmaceutically acceptable salt or diastereomer or enantiomer thereof, wherein:
  the dashed line is a single or a double bond;
  Y is H or $CH_3$;
  n is selected from the group consisting of 0, 1, 2, 3, or 4;
  $R_2$ is selected from the group consisting of H, $C_1$-$C_6$ alkyl, hydroxyalkyl, phenyl or biphenyl;
  $R_3$ is selected form the group consisting of H, $C(O)R_5$, $SO_2R_5$, $C_1$-$C_6$ alkyl;
  $R_5$ is $C_1$-$C_6$ alkyl, haloalkyl including trifluoromethyl, aryl or heteroaryl;
  $R_6$ is $CO_2H$, $CH_3$, $CO_2R_2$, $CH_2OR_2$, $CONR_2R_3$ or tetrazol-5-yl;
  $R_7$ is selected from the group consisting of H, $CF_3$, $OCH_3$; and
  $R_8$ is selected form the group consisting of H and $OCH_3$.

Some of the compounds of the present invention are diastereomers yet have very different activities, see Examples 9 and 10 and 12 and 13 in Table 1.

Some exemplary embodiments of the present invention are included in the following embodiments:

EMBODIMENT 1

A compound selected from the group comprising the following structure:

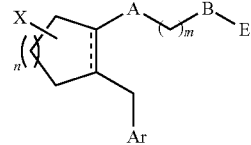

or a pharmaceutically acceptable salt or diastereomer or enantiomer thereof, wherein:
  n is 0, 1, 2, 3, or 4;
  m is 0 or 1;
  a dashed line represents a single or a double bond;
  X is zero, one or two substituents on the cycloalkane or cycloalkene ring, said substituents are selected from the group consisting of H, lower alkyl, hydroxyalkyl, aryl, halogen, cycloalkene, OR, $CF_3$, C(O)R, $COCF_3$, $SO_2N(R)_2$, $SO_2NH_2$, $NO_2$, and CN;
  A is selected form the group consisting of CH=CH, $CH_2CH_2$, C(O)NH, $C(O)NCH_3$, NHC(O), $CH_2O$, $CH_2N(H)$, $CH_2S$, $OCH_2$, $N(H)CH_2$, and $SCH_2$;

B is selected from the group consisting of arylene, heteroarylene, $CH_2$, $CH_2CH_2$, $CH_2CH_2CH_2$, $OCH_2$, $OCH_2CH_2$, and $CH_2OCH_2$;

E is selected from the group consisting of $CO_2R_2$, $CH_2OR_2$, $CONR_2R_3$ or tetrazol-5-yl;

Ar is selected from the groups consisting of unsubstituted or mono-, di-, or tri-substituted aryl and heteroaryl, said substituents chosen from the group consisting of lower alkyl, hydroxyalkyl, aryl, halogen, $OR_3$, $CF_3$, $C(O)R$, $COCF_3$, $SO_2N(R)_2$, $SO_2NH_2$, $NO_2$, and CN;

R is $C_1$-$C_6$ alkyl;

$R_2$ is selected from the group consisting of H, $C_1$-$C_6$ alkyl, hydroxyalkyl, phenyl or biphenyl;

$R_3$ is selected form the group consisting of H, $C(O)R_5$, $SO_2R_5$, $C_1$-$C_6$ alkyl; and $R_5$ is $C_1$-$C_6$ alkyl, haloalkyl including trifluoromethyl, aryl or heteroaryl.

EMBODIMENT 2

The compound of embodiment 1, wherein A is C(O)NH, m is 1, B is arylene and E is selected from the group consisting of $CO_2R_2$, $CH_2OR_2$, $CONR_2R_3$ and tetrazol-5-yl.

EMBODIMENT 3

The compound of embodiment 2 wherein B is arylene and E is $CO_2H$, n is 0 and Ar is aryl.

EMBODIMENT 4

The compound of embodiment 3 wherein aryl is phenyl and is di-substituted with $OCH_3$ and n is 0 or 1.

EMBODIMENT 5

The compound of embodiment 3 wherein n is 0 or 1 and Ar is selected from the group consisting of

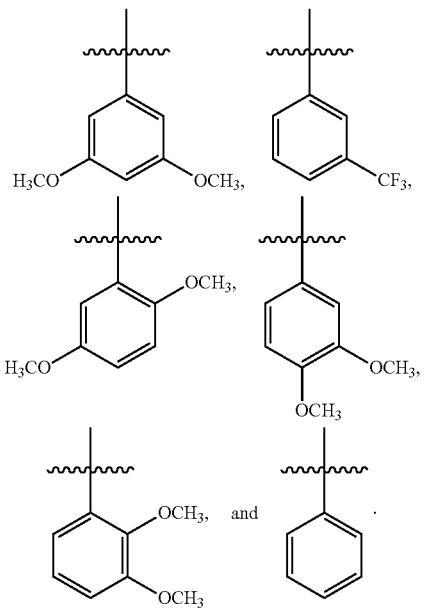

EMBODIMENT 6

The compound of embodiment 5 wherein Ar is

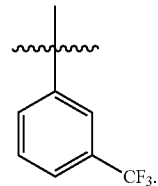

EMBODIMENT 7

The compound of embodiment 1 wherein n is 1 and the dashed line represents a double bond and Ar is

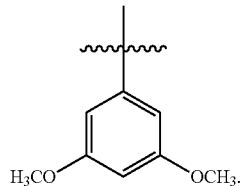

EMBODIMENT 8

The compound of embodiment 1 wherein n is 1 and the dashed line represents a single bond and Ar is

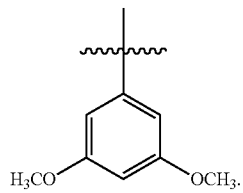 [SMILES: *c1cc(OC)cc(OC)c1]

EMBODIMENT 9

The compound of embodiment 1 wherein n is 2 and the dashed line represents a double bond and Ar is

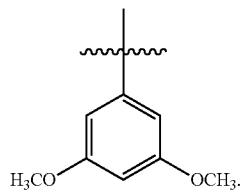

EMBODIMENT 10

The compound of embodiment 1 wherein n is 2 and the dashed line represents a single bond and Ar is

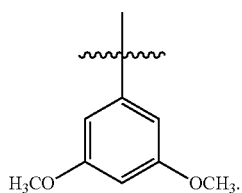

EMBODIMENT 11

The compound of embodiment 1, comprising the following structure:

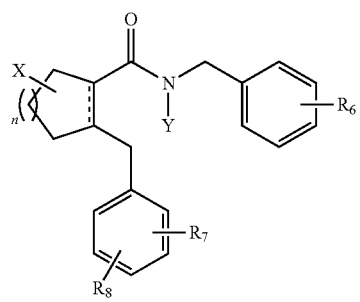

or a pharmaceutically acceptable salt or diastereomer or enentiomer thereof, wherein:

the dashed line is a single or a double bond;

Y is H or $CH_3$;

X is zero (meaning not present), one or two substituents on the cycloalkane or cycloalkene ring, said substituents chosen from the group consisting of H, $C_1$-$C_6$ alkyl, hydroxyalkyl, aryl, halogen, cycloalkene, OR, $CF_3$, C(O)R, $COCF_3$, $SO_2N(R)_2$, $SO_2NH_2$, $NO_2$, and CN;

n is selected from the group consisting of 0, 1, 2, 3, or 4;

R is $C_1$-$C_6$ alkyl;

$R_2$ is selected from the group consisting of H, $C_1$-$C_6$ alkyl, hydroxyalkyl, phenyl or biphenyl;

$R_3$ is selected form the group consisting of H, C(O)$R_5$, $SO_2R_5$, $C_1$-$C_6$ alkyl;

$R_5$ is $C_1$-$C_6$ alkyl, haloalkyl including trifluoromethyl, aryl or heteroaryl;

$R_6$ is $CO_2H$, $CH_3$, $CO_2R_2$, $CH_2OR_2$, $CONR_2R_3$ or tetrazol-5-yl;

$R_7$ is selected from the group consisting of H, $CF_3$, $OCH_3$; and $R_8$ is selected form the group consisting of H and $OCH_3$.

EMBODIMENT 12

The compound of embodiment 11, wherein $R_6$ is $CO_2H$ and n is selected from the group consisting of 0, 1 and 2.

EMBODIMENT 13

The compound of embodiment 11, wherein n is selected from the group consisting of 0, 1 and 2 and the dashed line represents a double bond.

EMBODIMENT 14

The compound of embodiment 13, wherein and $R_7$ and $R_8$ are $OCH_3$.

EMBODIMENT 15

The compound of embodiment 13, wherein $R_7$ is $CF_3$ and $R_8$ is H.

EMBODIMENT 16

The compound of embodiment 11 wherein n is selected from the group consisting of 1 and 2.

EMBODIMENT 17

The compound of embodiment 11 wherein the dashed line represents a single bond.

EMBODIMENT 18

The compound of embodiment 11 wherein n is selected from the group consisting of 3 and 4.

EMBODIMENT 19

The compound of embodiment 11 wherein $R_7$ and $R_8$ are $OCH_3$.

EMBODIMENT 20

The compound of embodiment 1 selected from the group consisting of

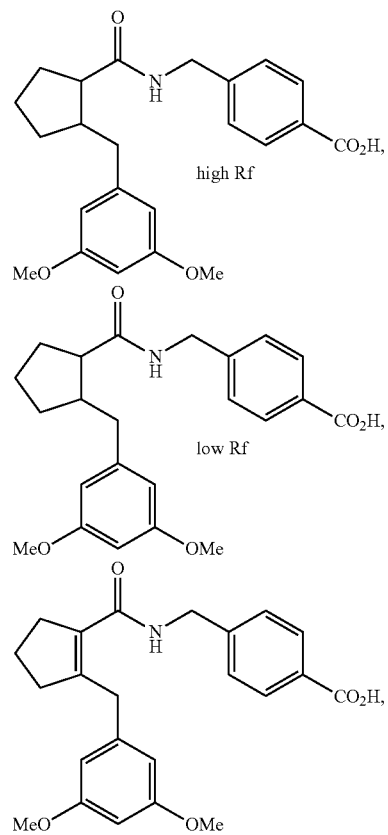

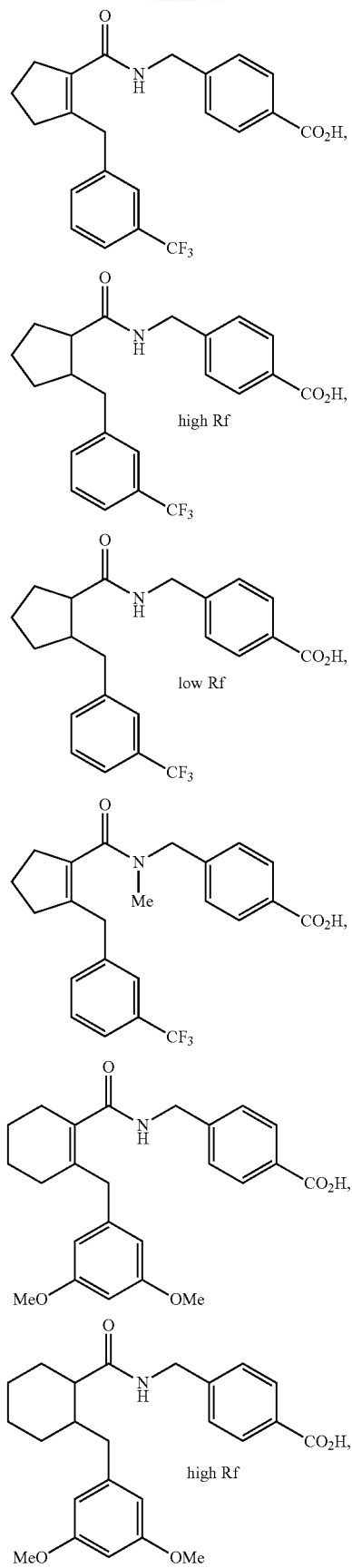
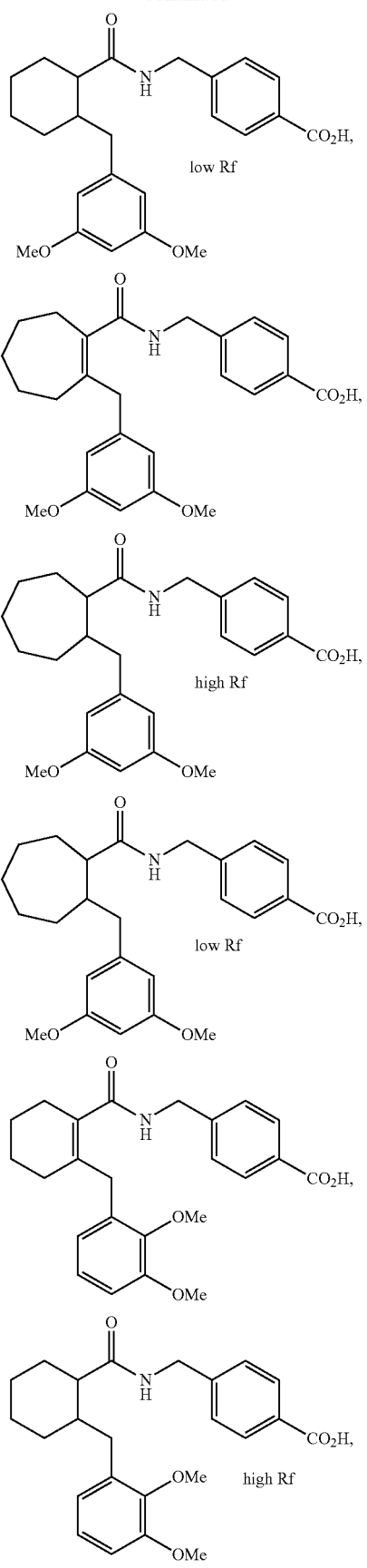

-continued
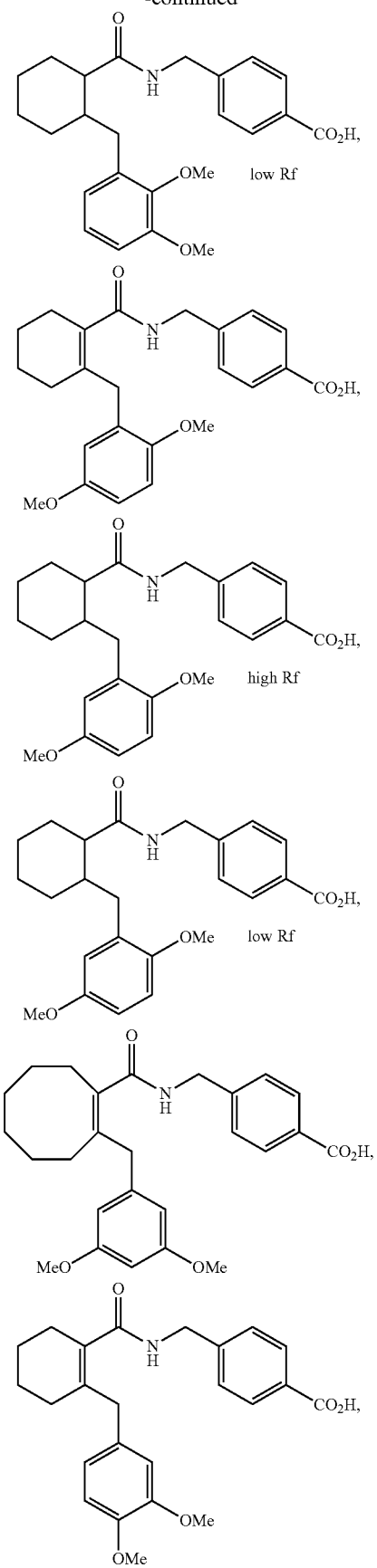
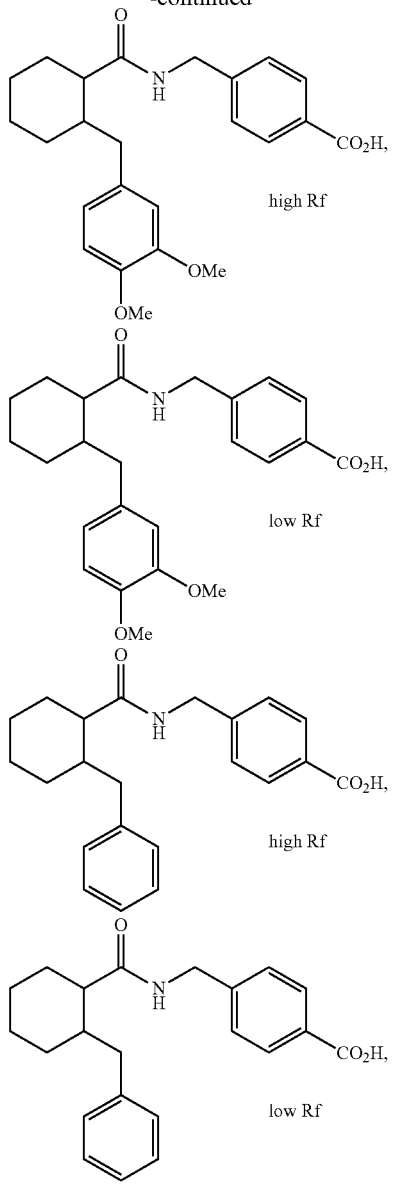
and pharmaceutically acceptable salts, diastereomers, and enantiomers thereof.
EMBODIMENT 21
The compound of embodiment 1, comprising the following structure:
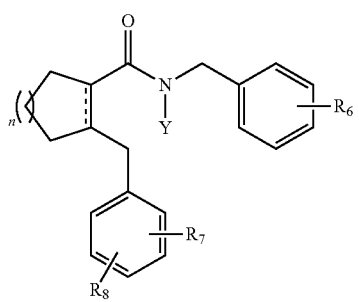

or a pharmaceutically acceptable salt or diastereomer or enantiomer thereof wherein:
the dashed line represents a single or double bond;
Y is H or $CH_3$;
$R_6$ is $CO_2H$;
n is 0, 1, 2, 3 or 4;
$R_7$ is selected from the group consisting of H, $OCH_3$ and $CF_3$;
$R_8$ is selected form the group consisting of H and OCH3.

EMBODIMENT 22

The compound of embodiments 11 and 21, wherein n is 1, 2 or 3, $R_6$ is $CO_2H$, Y is H, and the dashed line represents a single bond.

EMBODIMENT 23

The compound of embodiments 11 and 22, wherein $R_7$ and $R_8$ are $OCH_3$.

EMBODIMENT 24

The compound of embodiments 11 and 22, wherein $R_7$ is $CF_3$ and $R_8$ is H.

EMBODIMENT 25

The compound of embodiments 11 and 21, wherein n is 1, $R_6$ is $CO_2H$, Y is H, and the dashed line represents a double bond.

EMBODIMENT 26

The compound of embodiments 11 and 25, wherein and $R_7$ and $R_8$ are $OCH_3$.

EMBODIMENT 27

The compound of embodiments 11 and 22, wherein Y is H, $R_7$ is $CF_3$ and $R_8$ is H.

EMBODIMENT 28

The compound of embodiment 21, wherein Y is $CH_3$, $R_6$ is $CO_2H$, $R_7$ is $CF_3$ and $R_8$ is H.

EMBODIMENT 29

The compound of embodiment 11 and 21 wherein n is 4, Y is H, the dashed line represents a double bond and $R_7$ and $R_8$ are $OCH_3$.

EMBODIMENT 30

Use of the compounds of embodiments 1, 11, 20 and 21 in the treatment of low bone mass, particularly osteoporosis, frailty, an osteoporotic fracture, a bone defect, childhood idiopathic bone loss, alveolar bone loss, mandibular bone loss, bone fracture, osteotomy, bone loss associated with periodontitis, or prosthetic ingrowth, inducing bone formation, protection against inflammatory bowel disease, facilitate Langerhans cell migration and maturation, and mediate joint inflammation.

EMBODIMENT 31

Use of the compounds of embodiments 1, 11, 20 and 21 in the prophylaxis and/or treatment of autoimmune disorders such as amyotrophic lateral sclerosis, multiple sclerosis, inflammatory bowel disease, Sjoegren's syndrome, arthritis, rheumatoid arthritis, systemic lupus erythematosus, post-transplantation graft rejection, asthma, abnormal bone formation, neurocyte death, pulmopathy, hepatopathy, acute hepatitis, nephritis, renal insufficiency, hypertension, myocardial ischemia, systemic inflammatory syndrome, pain induced by ambustion, sepsis, hemophagocytosis syndrome, macrophage activation syndrome, Still's diseases, Kawasaki diseases, burns, systemic granuloma, ulcerative colitis, Crohn's diseases, hypercytokinemia at dialysis and multiple organ failure and shock, esophageal ulcers, alcohol gastropathy, duodenal ulcers, non-steroidal anti-inflammatory drug-induced gastroenteropathy and intestinal ischemia.

EMBODIMENT 32

Use of the compounds of embodiments 1, 11, 20 and 21 in the suppression of innate immunity and to down regulate the proliferation and activation of CD4+ T cells and to down regulate a T or B cell response.

EMBODIMENT 33

Use of the compounds of embodiments 1, 11, 20 and 21 in the treatment of acute hepatitis, asthma, bronchitis, burn, chronic obstructive respiratory diseases, Crohn's disease, digestive ulcer, glaucoma (and other diseases related to elevated intraocular pressure), hemophagous syndrome, hepatopathy, hypercytokinemia at dialysis, hypertension, immunological diseases (autoimmune diseases, organ transplantation, etc.), inflammation (such as rheumatoid arthritis), Kawasaki disease, liver injury, macrophage activation syndrome, myocardial ischemia, nephritis, nerve cell death, osteoporosis and diseases associated with bone disorders, premature birth, pulmonary emphysema, pulmonary fibrosis, pulmonary injury, renal failure, sepsis, sexual dysfunction, shock, sleep disorder, Still disease, stomatitis, systemic granuloma, systemic inflammatory syndrome, thrombosis and stroke, and ulcerative colitis.

EMBODIMENT 34

The compounds of embodiments 1, 11, 20 and 21 which are useful as $EP_4$ agonists and/or antagonists.

EMBODIMENT 35

The compounds of embodiments 1, 11, 20 and 21 which are useful for treating pathological conditions associated with the activity of the $EP_4$ receptor.

EMBODIMENT 36

A method of treating a skin blemish comprising administering to a subject in need thereof a therapeutically effective amount of a compound selected from embodiments 1, 11, 20 and 21.

EMBODIMENT 37

The method of embodiment 36, wherein the skin blemish is a flesh wound, scar, or wrinkle.

EMBODIMENT 38

The method of embodiment 37, wherein the skin blemish is a scar.

EMBODIMENT 39

The method of embodiment 36, wherein the administration minimizes scar formation.

EMBODIMENT 40

The method of embodiment 36, wherein the administration prevents scar formation.

EMBODIMENT 41

The method of embodiment 38, wherein the administration reduces formation of a scar type selected from the group consisting of hypertrophic scar, recessed scar, stretch mark, and a combination thereof.

EMBODIMENT 42

The method of embodiment 37, wherein the skin blemish is a flesh wound.

EMBODIMENT 43

The method of embodiment 42, wherein a cause of the flesh wound is selected from the group consisting of an incision, a laceration, a thermal burn, a chemical burn, an abrasion, a puncture wound, and/or a combination thereof.

EMBODIMENT 44

Use of the compounds of embodiments 1, 11, 20 and 21 in the manufacture of a medicament for the prophylaxis and/or treatment of autoimmune disorders such as amyotrophic lateral sclerosis, multiple sclerosis, inflammatory bowel disease, Sjoegren's syndrome, arthritis, rheumatoid arthritis, systemic lupus erythematosus, post-transplantation graft rejection, asthma, abnormal bone formation, neurocyte death, pulmopathy, hepatopathy, acute hepatitis, nephritis, renal insufficiency, hypertension, myocardial ischemia, systemic inflammatory syndrome, pain induced by ambustion, sepsis, hemophagocytosis syndrome, macrophage activation syndrome, Still's diseases, Kawasaki diseases, burns, systemic granuloma, ulcerative colitis, Crohn's diseases, hypercytokinemia at dialysis and multiple organ failure and shock, esophageal ulcers, alcohol gastropathy, duodenal ulcers, non-steroidal anti-inflammatory drug-induced gastroenteropathy and intestinal ischemia.

EMBODIMENT 45

Use of the compounds of embodiments 1, 11, 20 and 21 in the manufacture of a medicament for suppression of innate immunity and to down regulate the proliferation and activation of CD4+ T cells and to down regulate a T or B cell response.

EMBODIMENT 46

Use of the compounds of embodiments 1, 11, 20 and 21 in the manufacture of a medicament for the treatment of acute hepatitis, asthma, bronchitis, burn, chronic obstructive respiratory diseases, Crohn's disease, digestive ulcer, glaucoma (and other diseases related to elevated intraocular pressure), hemophagous syndrome, hepatopathy, hypercytokinemia at dialysis, hypertension, immunological diseases (autoimmune diseases, organ transplantation, etc.), inflammation (such as rheumatoid arthritis), Kawasaki disease, liver injury, macrophage activation syndrome, myocardial ischemia, nephritis, nerve cell death, osteoporosis and diseases associated with bone disorders, premature birth, pulmonary emphysema, pulmonary fibrosis, pulmonary injury, renal failure, sepsis, sexual dysfunction, shock, sleep disorder, Still disease, stomatitis, systemic granuloma, systemic inflammatory syndrome, thrombosis and stroke, and ulcerative colitis.

EMBODIMENT 47

A pharmaceutical composition comprising a compound of embodiment 1 and a pharmaceutically acceptable composition.

EMBODIMENT 48

A method of treating glaucoma, the method comprising administering an effective amount of the compound of embodiment 1 to an individual in need thereof.

DETAILED DESCRIPTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting.

As used herein "alkane" refers to compounds consisting of only hydrogen and carbon, fully saturated and containing only single bonds.

As used herein, "alkyl" refers to straight or branched chain hydrocarbyl groups having from 1 to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. For example, the term "alkyl" can refer to a sub-range between $C_1$-$C_{100}$ (e.g. $C_1$-$C_6$). "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)$R_9$, —CH$_2$O$R_9$, —C(O)—, —S—, —S(O)$_2$, —OC(O)—O—, wherein $R_9$ is H or lower alkyl, acyl, oxyacyl, carboxyl, carbamate, sulfonyl, sulfonamide, sulfuryl, and the like. As used herein, "lower alkyl" refers to alkyl moieties having from 1 to about 6 carbon atoms.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 5 up to 14 (e.g., phenyl) carbon atoms and "substituted aryl" refers to aryl groups further bearing one or more substituents as set forth above.

As used herein "arylene" and "heteroarylene" refer to an aryl ring or ring system or a heteroaryl ring or ring system which connects two other parts of a molecule, i.e. the two parts are bonded to the ring or ring system in two distinct ring positions. Arylene and heteroarylene may be substituted or unsubstituted. Unsubstituted arylene and heteroarylene have no substituents other than the two parts of the molecule it connects. Substituted arylene and heteroarylene have substituents in addition to the two parts of the molecule it connects.

An "effective amount" of a compound is an amount sufficient to contribute to the treatment, prevention (e.g. prophylaxis), or reduction of a symptom or symptoms of a disease. Where recited in reference to a disease treatment, an "effective amount" may also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) a disease, disorder or condition, or reducing the likelihood of the onset (or reoccurrence) of a disease, disorder or condition or symptoms thereof. The full prophylactic effect does not necessarily occur by administration of one dose, and may occur only after administration of a series of doses. Thus, a prophylactically effective amount may be administered in one or more administrations.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heteroaryl" refers to heteroaryl groups further bearing one or more substituents as set forth above.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "halogen" or "halide" refers to fluoride, chloride, bromide or iodide. "Fluoride, chloride, bromide or iodide" may also be referred to as "fluoro", "chloro", "bromo", or "iodo".

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

As used herein, "diastereomers" are stereoisomers in which asymmetric centers are different but which are not enantiomers.

In particular, a skilled person will realize that even if the absolute stereochemistry of a particular stereoisomer (e.g. an enantiomer or diastereomer) of a molecule is not known, that particular stereoisomer can be distinguished from the other stereoisomers by use of other techniques (e.g. polarimetry, nuclear magnetic resonance spectroscopy, chromatography, and others identifiable to a skilled person).

In particular, one exemplary method of distinguishing stereoisomers when the absolute stereochemistry of each stereoisomer is not known is chromatography such as high pressure liquid chromatography (HPLC) or thin-layer chromatograph (TLC). In particular, two or more stereoisomers such as diastereomers can be separated and characterized by their retention times and of $R_f$ values, which would be expected to be replicable by using the same chromatographic conditions (e.g. flow rate, column material, TLC stationary phase, solvent systems/gradient profiles, and others identifiable to a skilled person). In particular, a skilled person will realize that even when the exact relative retention times and/or $R_f$ values of one or more stereoisomers is not replicated (e.g. due to slight variations in the chromatographic parameters and/or chromatographic equipment), a stereoisomer with a shorter retention time can be said to be "faster eluting" and a stereoisomer with a linger retention time can be said to be "slower eluting", and similarly, a stereoisomer with smaller $R_f$ value can be said to have a "low $R_f$" and a stereoisomer with a larger $R_f$ value can be said to have a "high $R_f$".

A skilled person will realize that once two or more stereoisomers are distinguished by a technique such as chromatography (e.g. HPLC and/or TLC), the absolute stereochemistry of the stereoisomers can be determined by techniques or combinations of techniques identifiable to a skilled person (e.g. x-ray crystallography, vibrational circular dichroism, nuclear magnetic resonance, total synthesis, and others identifiable to a skilled person).

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring. The term "pharmaceutically acceptable salt" is also meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66:1-19) which is incorporated by reference. Certain specific compounds of the present invention may contain both basic and acidic functionalities that allow the compounds to be converted into either base or acid addition salts.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group or to mean compounds which are converted or metabolized into an active compound, e.g., by covalently bonded carriers, which are capable of releasing an active ingredient when the prodrug is administered to a subject (e.g. mammalian subject). Generally, but not necessarily, a prodrug is inactive or less active than the therapeutically active compound to which it is converted.

The terms "treating" or "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination.

The present invention also provides compounds and methods for wound healing and scar reduction. The compounds and methods of the present invention include at least one EP4 agonist or antagonist. Wounds and or scars that can be treated by the compounds and methods of the invention can arise from events such as surgery, trauma, disease, mechanical injury, burn, radiation, poisoning, and the like. As used herein, the term "skin blemish" includes a flesh wound, scar, or wrinkle on any region of the skin of a body.

A "flesh wound" can be any area in which the structural integrity of the exterior surface of the skin is compromised. A flesh wound can be due to incision, laceration, abrasion, thermal burn, chemical burn, radiation or puncture of the skin. The wound can be superficial or extend to the deeper layers of the dermis, subcutaneous, deep fascia, muscle, bone or other internal organs.

A "scar" is an area of fibrous tissue (fibrosis) that replaces normal skin (or other tissue) after injury or disease. Scar types include hypertrophic scars, recessed scars, and stretch marks. Hypertrophic scars occur when the body overproduces collagen, which causes the scar to be raised above the surrounding skin. An example of a hypertrophic scar is a keloid scar. Atrophic, or recessed scars, have a sunken appearance and result when underlying support structure in the skin is lost. Stretch marks (striae) occur when skin is stretched rapidly (i.e., due to significant weight gain or growth spurt), or when skin is put under tension during the healing process, typically near a joint. As used herein, the term "scar" encompasses any type of scar in the skin due to any cause, as would be understood to a skilled person upon a reading of the present disclosure.

As used herein, the term "wrinkle" is a fold, ridge, crease, furrow, pit, crater, or sunken area in the skin that can be caused by habitual facial expressions, loss of collagen and/or elasticity due to aging, sun damage, smoking, poor hydration, and various other factors. A wrinkle can range from a deep crease to a fine line. Wrinkles occurring on any part of a body, in particular, wrinkles on head or neck of a subject are contemplated herein. Wrinkles that can be treated in accordance with the disclosure include, but are not limited to, a brow furrow, crows feet, nasolabial fold, one or more lines under the eyes or between the eye brows, and combinations thereof.

When the compounds are administered to treat a wound, the compounds promote normal healing compared to a wound without the administration. That is, the size (length, depth, height and/or width), character, color and/or texture of the treated wound more closely resemble normal, non-wounded tissue. In this regard, treatment of a wound with the disclosed compounds can prevent, minimize or improve the appearance of a scar formation resulting from healing of the wound. Further, when the disclosed compounds are administered to treat a wrinkle, the wrinkle is treated if the appearance or prominence of the wrinkle is visibly or clinically diminished. That is the length and/or depth is decreased compared to the wrinkle prior to treatment. Alternatively, treatment can comprise prevention of a wrinkle. In this regard, the disclosed compounds can be applied to a region of the skin that typically develops a wrinkle, such as a forehead, lips, eyelids, nasolabial fold, skin under an eye, or between the eye brows in order to prevent the development of a wrinkle.

The compounds of the prevent invention can be administered to prevent scar formation not associated with a wound, such as a stretch mark, or scars resulting from acne, chicken pox, measles or other disease states. In certain embodiments, the disclosed compounds are administered to the area of skin expansion in order to prevent formation of such scars. In these embodiments, the compounds can be administered to any region of a face, abdomen, breasts, arms, legs, buttocks, back, or any other area where the skin is susceptible to developing a scar.

The compounds can be administered prior to, concurrently with, and/or after the development of the skin blemish. For instance, the disclosed compounds can be administered prior to an incision, during a surgical procedure, and/or any time post-operatively, and then additionally administered after the procedure as the healing process occurs. In another example, the compounds can be administered during pregnancy to prevent stretch marks. Alternately, the compounds can be administered after the development of a blemish.

EXAMPLES

The following examples are intended only to illustrate the invention and should in no way be construed as limiting the invention.

Synthetic Procedures

Scheme 1 sets forth below outlines a synthetic route to the compound of the invention described in Examples 1 and 2:

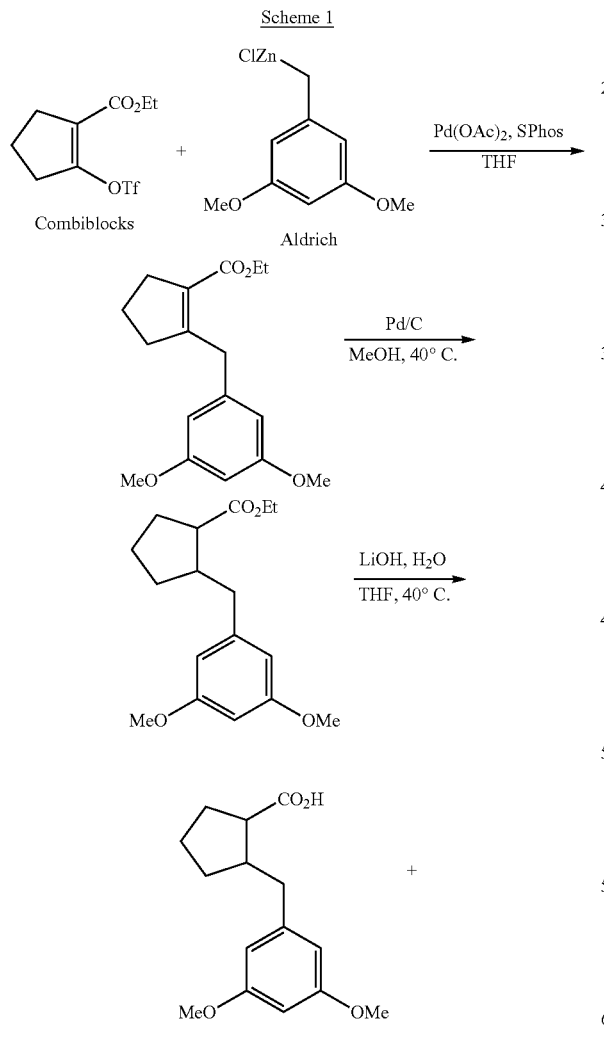

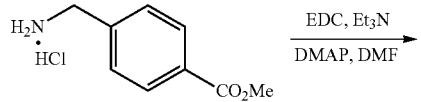

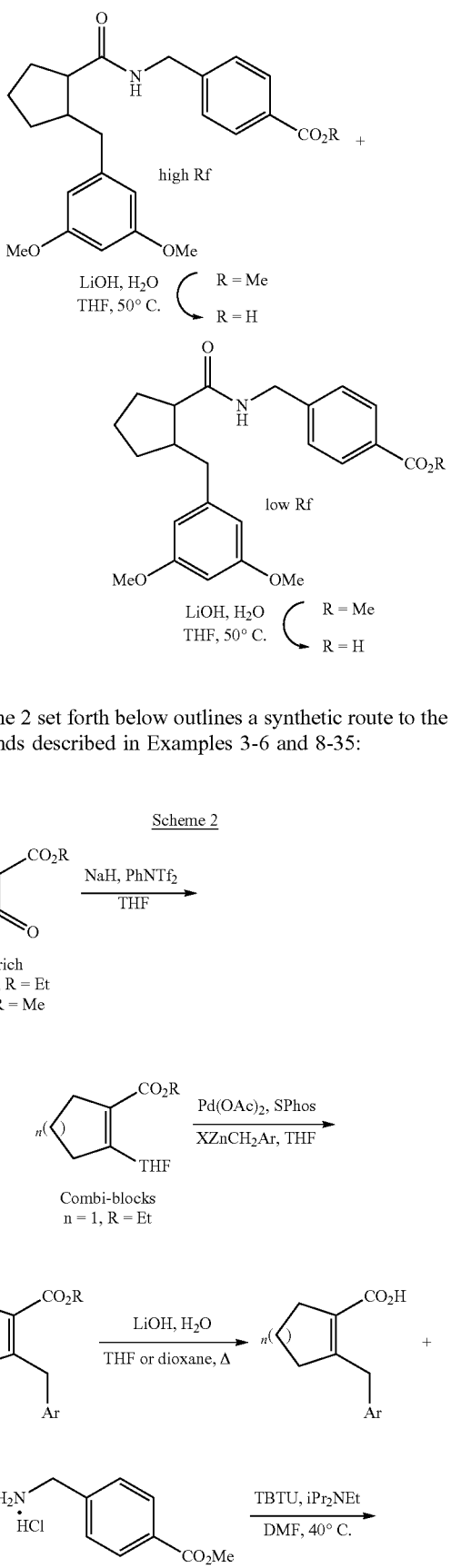

Scheme 2 set forth below outlines a synthetic route to the compounds described in Examples 3-6 and 8-35:

-continued
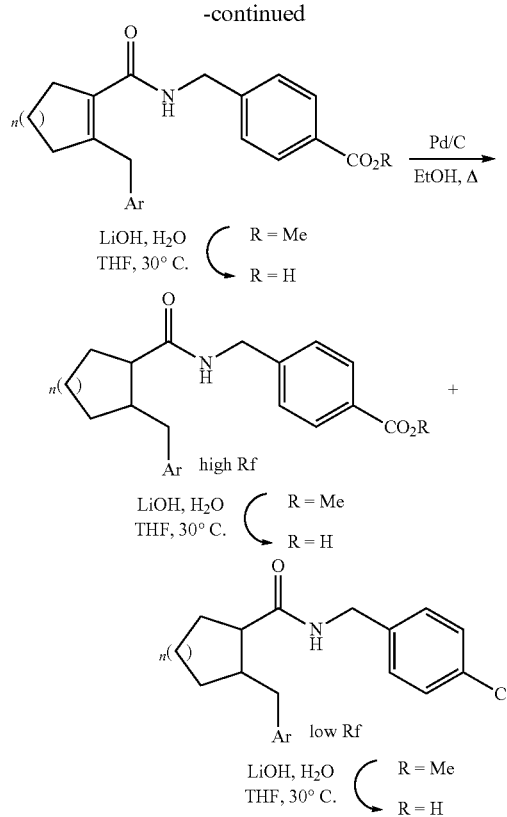
The following scheme (Scheme 3) sets forth a synthetic route to the compounds of the invention described in Example 7:
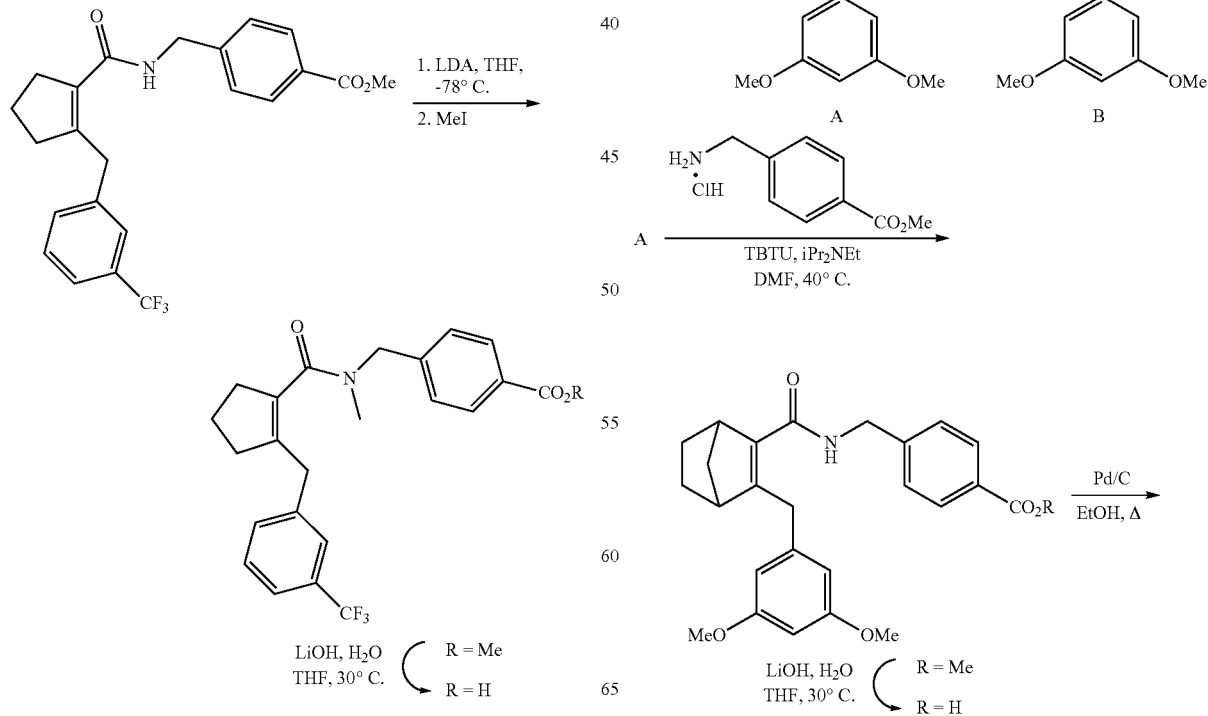
Scheme 4 set forth below outlines a synthetic route to the compound described in Examples 36-39:
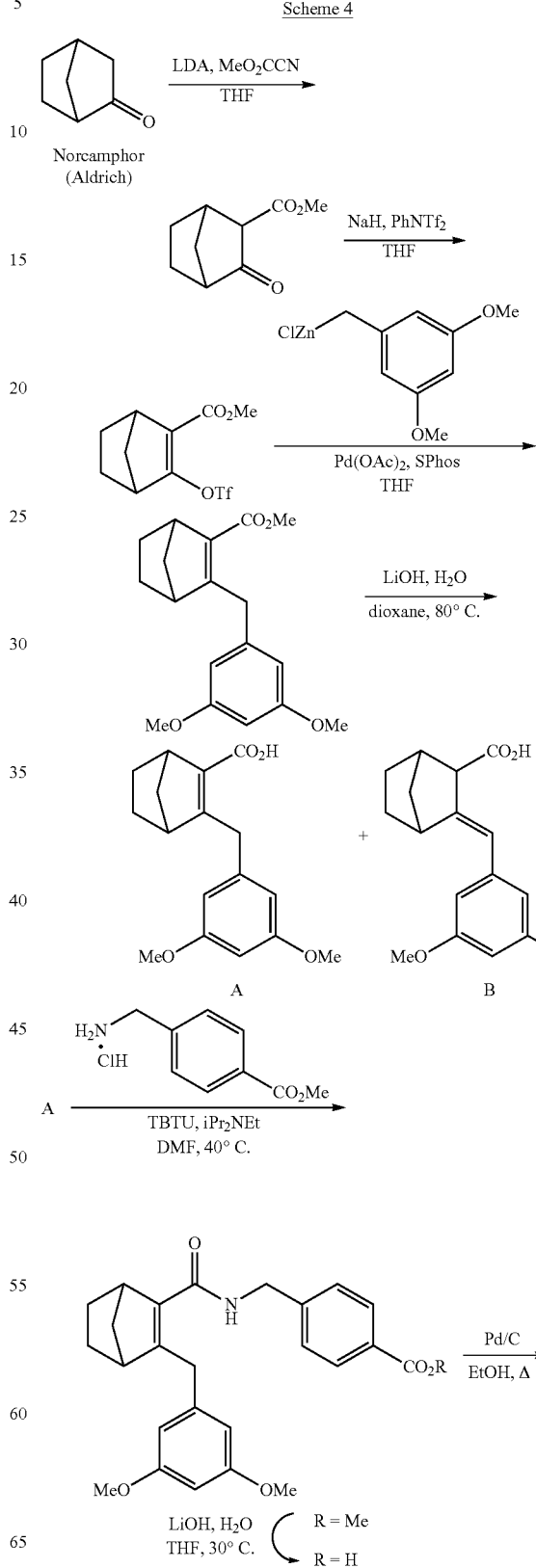

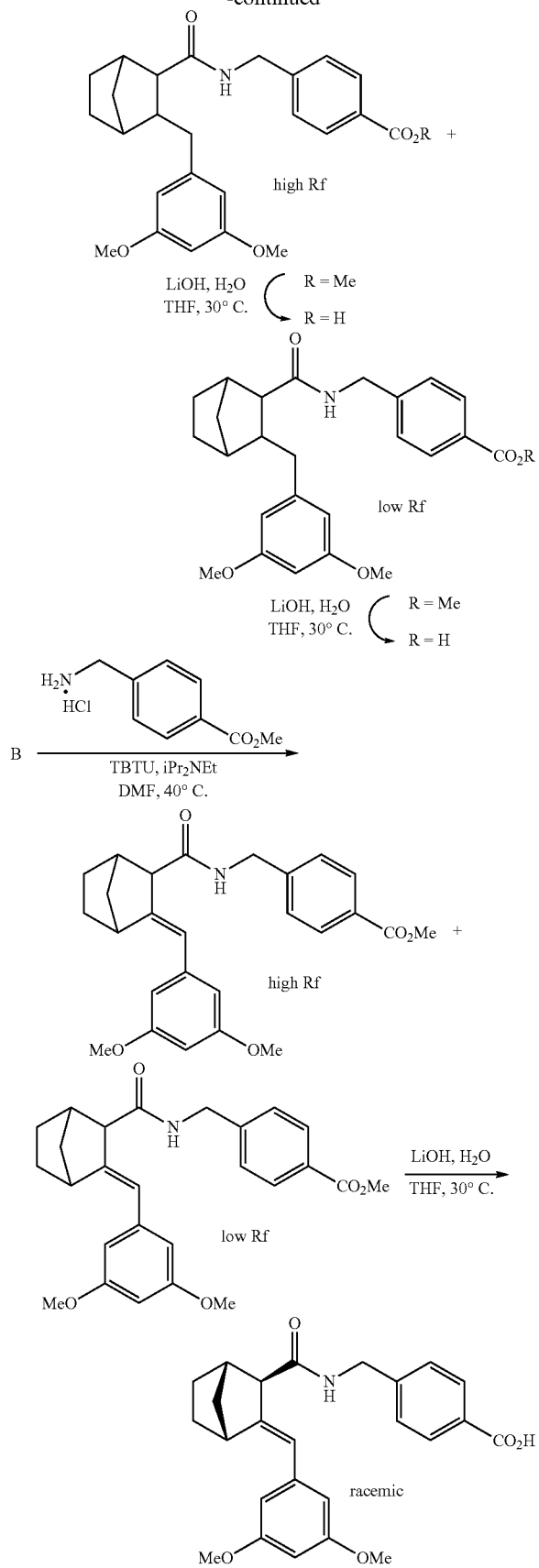

Example 1

4-((2-(3,5-Dimethoxybenzyl)cyclopentanecarbox-amido)methyl)benzoic acid (from high $R_f$ ester diastereomer)

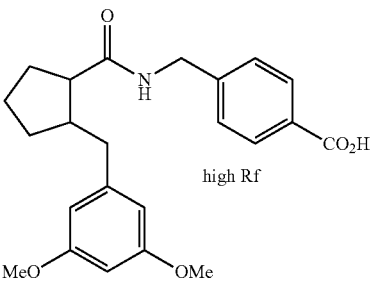 [SMILES: COc1cc(CC2CCCC2C(=O)NCc2ccc(C(=O)O)cc2)cc(OC)c1]

high Rf

Step 1. Ethyl 2-(3,5-dimethoxybenzyl)cyclopent-1-enecarboxylate

Palladium acetate (3.3 mg, 0.015 mmol) and SPhos (11.8 mg, 0.029 mmol) were added to a solution of ethyl 2-(((trifluoromethyl)sulfonyl)oxy)cyclopent-1-enecarboxylate (Combiblocks, Inc., 411 mg, 1.43 mmol) in THF (1.43 mL). The reaction mixture was purged with nitrogen and a solution of 3,5-dimethoxybenzylzinc chloride (Aldrich, 3.4 mL of a 0.5 M solution in THF, 1.7 mmol) was added drop-wise. After stirring at room temperature overnight, the reaction mixture was quenched with saturated aqueous $NH_4Cl$ (25 mL) and extracted with EtOAc (3×75 mL). The combined extracts were dried ($Na_2SO_4$), filtered and concentrated. The resulting crude residue was purified on a Teledyne-Isco Combiflash machine (40 g gold column, hexanes→50% EtOAc/hexanes, gradient), to afford 353 mg (85%) of ethyl 2-(3,5-dimethoxybenzyl)cyclopent-1-enecarboxylate.

Step 2. Ethyl 2-(3,5-dimethoxybenzyl)cyclopentanecarboxylate

Palladium on carbon (10 wt %, 5 mg) was added to a solution of ethyl 2-(3,5-dimethoxybenzyl)cyclopent-1-enecarboxylate (100 mg, 0.34 mmol) in methanol (3.4 mL). A hydrogen atmosphere was established by evacuating and refilling with hydrogen (3×). The reaction mixture placed in a 40° C. bath and stirred under a balloon of hydrogen overnight. The mixture was then cooled and filtered through celite, washing with excess methanol. The filtrate was concentrated in vacuo to afford 100 mg (quant.) of ethyl 2-(3,5-dimethoxybenzyl)cyclopentanecarboxylate.

Step 3. 2-(3,5-Dimethoxybenzyl)cyclopentanecarboxylic acid

Aqueous lithium hydroxide (1.7 mL of a 1.0 M solution, 1.7 mmol) was added to a solution of ethyl 2-(3,5-dimethoxybenzyl)cyclopentanecarboxylate (100 mg, 0.34 mmoL) in THF (3.4 mL) in a scintillation vial. The vial was heated at 60° C. for 3 days then cooled to room temperature. The organic solvent was removed under a stream of nitrogen, then the residue was diluted with water (5 mL), acidified with 1 N HCl (2 mL) and extracted with EtOAc (3×20 mL). The extracts were dried ($Na_2SO_4$), filtered and concentrated to afford 98 mg (quant.) of 2-(3,5-dimethoxybenzyl)cyclopentanecarboxylic acid.

Step 4. Methyl 4-((2-(3,5-dimethoxybenzyl)cyclopentanecarboxamido)methyl)benzoate Triethylamine (28 μL, 0.20 mmol), DMAP (56 mg, 0.45 mmol), methyl 4-(aminomethyl)benzoate hydrochloride (41 mg, 0.20 mmol) and N-(3-dimethylaminopropyl)-N'-ethylcarbodiimide hydrochloride (50 mg, 0.26 mmol) were added sequentially to a solution of 2-(3,5-dimethoxybenzyl)cyclopentanecarboxylic acid (52 mg, 0.20 mmol) in CH$_2$Cl$_2$ (2.0 mL). The heterogeneous mixture was allowed to stir at room temperature overnight, during which time the reaction became homogeneous. The reaction solution was treated with saturated aqueous NH$_4$Cl (10 mL) and extracted with EtOAc (3×20 mL). The combined extracts were dried (Na$_2$SO$_4$), filtered and concentrated. The resulting crude residue was purified on a Teledyne-Isco Combiflash machine (4 g gold column, hexanes→EtOAc, gradient), to afford 13 mg (16%) of methyl 4-((2-(3,5-dimethoxybenzyl)cyclopentanecarboxamido)methyl)benzoate (high R$_f$ diastereomer) and 3.6 mg (4%) of methyl 4-((2-(3,5-dimethoxybenzyl)cyclopentanecarboxamido)methyl)benzoate (low R$_f$ diastereomer).

Step 5. 4-((2-(3,5-Dimethoxybenzyl)cyclopentanecarboxamido)methyl)benzoic acid (from high R$_f$ ester diastereomer)

Aqueous lithium hydroxide (0.15 mL of a 1.0 M solution, 0.15 mmol) was added to a solution of methyl 4-((2-(3,5-dimethoxybenzyl)cyclopentanecarboxamido)methyl)benzoate (high R$_f$ diastereomer, 13 mg, 0.032 mmol) in THF (0.3 mL) in a 1-dram vial. The vial was heated at 50° C. overnight then cooled to room temperature. The organic solvent was removed under a stream of nitrogen, then the residue was diluted with water (0.5 mL), acidified with 1 N HCl (0.5 mL) and extracted with EtOAc (3×2 mL). The extracts were dried (Na$_2$SO$_4$), filtered and concentrated to afford 11 mg (88%) of the title compound.

Example 2

4-((2-(3,5-Dimethoxybenzyl)cyclopentanecarboxamido)methyl)benzoic acid (from low R$_f$ ester diastereomer, see Example 1)

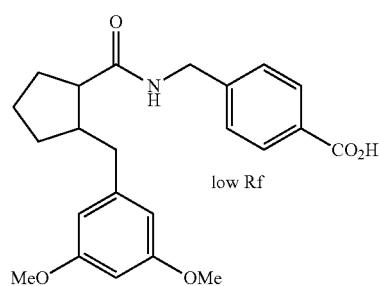 [SMILES: COc1cc(CC2CCCC2C(=O)NCc2ccc(C(=O)O)cc2)cc(OC)c1]

low Rf

In accordance with the procedure of Example 1, step 5, methyl 4-((2-(3,5-dimethoxybenzyl)cyclopentanecarboxamido)methyl)benzoate (low R$_f$ diastereomer, 3.6 mg, 0.009 mmol) was converted into 3 mg (86%) of the title compound.

Example 3

4-((2-(3,5-Dimethoxybenzyl)cyclopent-1-enecarboxamido)methyl)benzoic acid

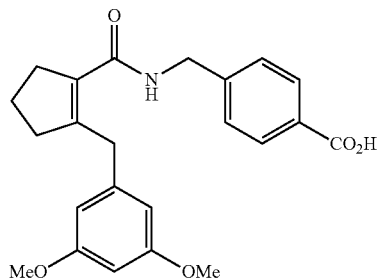 [SMILES: COc1cc(CC2=C(C(=O)NCc3ccc(C(=O)O)cc3)CCC2)cc(OC)c1]

Step 1.
2-(3,5-Dimethoxybenzyl)cyclopent-1-enecarboxylic acid

Aqueous lithium hydroxide (4.1 mL of a 1.0 M solution, 4.1 mmol) was added to a solution of ethyl 2-(3,5-dimethoxybenzyl)cyclopent-1-enecarboxylate (68.7 mg, 0.237 mmol) in THF (4.1 mL). The vial was heated at 60° C. for 24 h after which time TLC analysis showed little if any reaction had occurred. A second portion of lithium hydroxide (351 mg, 8.20 mmol) was added, and the mixture was stirred for an additional 18 h at 60° C. The mixture was then cooled to room temperature, acidified with 1 N HCl and extracted with CH$_2$Cl$_2$ (3×). The extracts were dried (MgSO$_4$), filtered and concentrated. The resulting crude residue was purified on a Teledyne-Isco Combiflash machine (4 g gold column, 5% EtOAc/hexanes→60% EtOAc/hexanes, gradient), to afford 22.5 mg (36%) of 2-(3,5-dimethoxybenzyl)cyclopent-1-enecarboxylic acid.

Step 2. Methyl 4-((2-(3,5-dimethoxybenzyl)cyclopent-1-enecarboxamido) methyl)benzoate TBTU (O-Benzotriazol-1-yl-N,N,N',N'-tetramethyluronium hexafluorborate (28.0 mg, 0.0863 mmol), methyl 4-(aminomethyl)benzoate hydrochloride (18.1 mg, 0.0870 mmol) and diisopropylethylamine (45 μL, 0.26 mmol), were added to a solution of 2-(3,5-dimethoxybenzyl)cyclopent-1-enecarboxylic acid (22.5 mg, 0.858 mmol) in DMF (0.43 mmol). After stirring at 40° C. for 18 h, the reaction mixture was diluted with EtOAc and washed with 1 N HCl (2×), 1 N NaOH (2×) and brine. The organic phase was dried (MgSO$_4$), filtered and concentrated in vacuo to afford 35 mg (99%) of methyl 4-((2-(3,5-dimethoxybenzyl)cyclopent-1-enecarboxamido)methyl)benzoate as a white solid.

Step 3. 4-((2-(3,5-Dimethoxybenzyl)cyclopent-1-enecarboxamido)methyl)benzoic acid Water (363 μL) and aqueous lithium hydroxide (0.56 mL of a 1.0 M solution, 0.56 mmol) were added to a solution of methyl 4-((2-(3,5-dimethoxybenzyl)cyclopent-1-enecarboxamido)methyl)benzoate (11.0 mg, 0.0269 mmol) in THF (0.75 mL). After stirring at 30° C. for 18 h, the mixture was cooled, acidified with 1 N HCl and extracted with CH$_2$Cl$_2$ (3×). The combined extracts were dried (MgSO$_4$), filtered and concentrated. The resulting crude residue was purified on a Teledyne-Isco Combiflash machine (4 g gold column, 30% EtOAc/hexanes→60% EtOAc/hexanes (both solvents containing 0.5% AcOH), gradient), to afford 5.9 mg (55%) of the title compound.

Example 4

4-((2-(3-(Trifluoromethyl)benzyl)cyclopent-1-enecarboxamido)methyl)benzoic acid

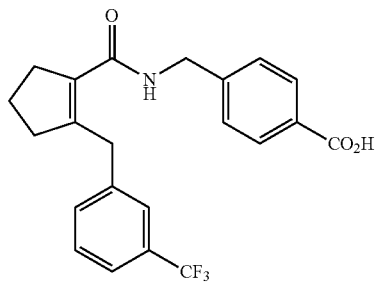 [SMILES: O=C(NCc1ccc(C(=O)O)cc1)C1=C(Cc2cccc(C(F)(F)F)c2)CCC1]

Step 1. Ethyl 2-(3-(trifluoromethyl)benzyl)cyclopent-1-enecarboxylate

Palladium acetate (3.1 mg, 0.014 mmol) and SPhos (10.9 mg, 0.0258 mmol) were added to a solution of ethyl 2-(((trifluoromethyl)sulfonyl)oxy)cyclopent-1-enecarboxylate (Combiblocks, Inc., 380 mg, 1.25 mmol) in THF (1.3 mL). The reaction mixture was purged with nitrogen for 10 min and a solution of 3-trifluormethylbenzylzinc chloride (Aldrich, 3.1 mL of a 0.5 M solution in THF, 1.6 mmol) was added drop-wise. After stirring at room temperature overnight, the reaction mixture was quenched with saturated aqueous $NH_4Cl$ and extracted with EtOAc (3×). The combined extracts were dried ($MgSO_4$), filtered and concentrated. The resulting crude residue was purified on a Teledyne-Isco Combiflash machine (40 g gold column, hexanes→15% EtOAc/hexanes, gradient), to afford 342 mg (92%) of ethyl 2-(3-(trifluoromethyl)benzyl)cyclopent-1-enecarboxylate.

Step 2. 2-(3-(Trifluoromethyl)benzyl)cyclopent-1-enecarboxylic acid

Aqueous lithium hydroxide (6.5 mL of a 3.0 M solution, 20 mmol) was added to a solution of ethyl 2-(3-(trifluoromethyl)benzyl)cyclopent-1-enecarboxylate (111 mg, 0.373 mmol) in 1,4-dioxane (6.5 mL). The reaction mixture was heated at 70° C. for 18 h then cooled to room temperature. The reaction mixture was acidified with 1 N HCl and extracted with $CH_2Cl_2$ (3×). The extracts were dried ($MgSO_4$), filtered and concentrated in vacuo. The resulting crude residue was purified on a Teledyne-Isco Combiflash machine (12 g gold column, 5% EtOAc/hexanes→40% EtOAc/hexanes, gradient), to afford 83.1 mg (83%) of 2-(3-(trifluoromethyl)benzyl)cyclopent-1-enecarboxylic acid.

Step 3. Methyl 4-((2-(3-(trifluoromethyl)benzyl) cyclopent-1-enecarboxamido) methyl)benzoate In accordance with the procedure of Example 3, step 2, 2-(3-(trifluoromethyl)benzyl)cyclopent-1-enecarboxylic acid (81.7 mg, 0.302 mmol) and methyl 4-(aminomethyl) benzoate hydrochloride (63.1 mg, 0.304 mmol) were converted into 126 mg (quant.) of methyl 4-((2-(3-(trifluoromethyl)benzyl)cyclopent-1-enecarboxamido)methyl) benzoate.

Step 4. 4-((2-(3-(Trifluoromethyl)benzyl)cyclopent-1-enecarboxamido)methyl)benzoic acid In accordance with the procedure of Example 3, step 3, of methyl 4-((2-(3-(trifluoromethyl)benzyl)cyclopent-1-enecarboxamido)methyl)benzoate (10.4 mg, 0.0249 mmol) was converted into 6.8 mg (68%) of the title compound.

Example 5

4-((2-(3-(Trifluoromethyl)benzyl)cyclopentanecarboxamido)methyl)benzoic acid (from high $R_f$ ester diastereomer, see Example 4)

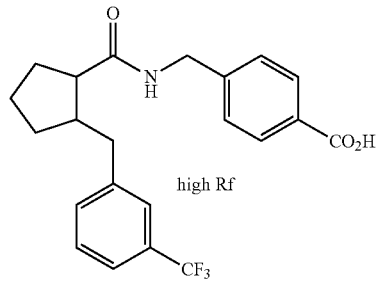 [SMILES: O=C(O)c1ccc(CNC(=O)C2CCCC2Cc2cccc(C(F)(F)F)c2)cc1]

high Rf

Step 1. Methyl 4-((2-(3-(trifluoromethyl)benzyl) cyclopentanecarboxamido)methyl)benzoate Palladium on carbon (10 wt %, 8.7 mg) was added to a solution of methyl 4-((2-(3-(trifluoromethyl)benzyl)cyclopent-1-enecarboxamido)methyl)benzoate (47.9 mg, 0.115 mmol) in ethanol (1.7 mL). A hydrogen atmosphere was established by evacuating and refilling with hydrogen (3×). The reaction mixture placed in a 40° C. bath and stirred under a balloon of hydrogen overnight. The mixture was then cooled and filtered through celite, washing with excess ethanol and the filtrate was concentrated in vacuo. The resulting crude residue was purified on a Teledyne-Isco Combiflash machine (4 g gold column, 20% EtOAc/hexanes→50% EtOAc/hexanes, gradient), to afford 30.5 mg (63%) of methyl 4-((2-(3-(trifluoromethyl)benzyl)cyclopentanecarboxamido)methyl)benzoate (high $R_f$ diastereomer) and 13.8 mg (29%) of methyl 4-((2-(3-(trifluoromethyl) benzyl) cyclopentanecarboxamido) methyl)benzoate (low $R_f$ diastereomer).

Step 2. 4-((2-(3-(Trifluoromethyl)benzyl)cyclopentanecarboxamido)methyl)benzoic acid (from high $R_f$ ester diastereomer)

In accordance with the procedure of Example 3, step 3, methyl 4-((2-(3-(trifluoromethyl)benzyl)cyclopentanecarboxamido)methyl)benzoate (high $R_f$ diastereomer, 17.2 mg, 0.0410 mmol) was converted into 8.2 mg (49%) of the title compound.

Example 6

4-((2-(3-(Trifluoromethyl)benzyl)cyclopentanecarboxamido)methyl)benzoic acid (from low $R_f$ ester diastereomer, see Example 5)

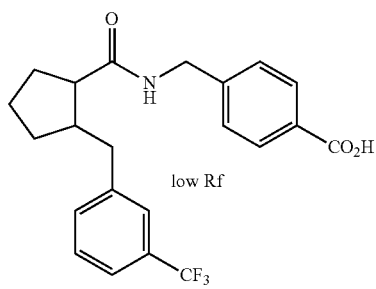 [SMILES: O=C(O)c1ccc(CNC(=O)C2CCCC2Cc2cccc(C(F)(F)F)c2)cc1]

low Rf

In accordance with the procedure of Example 3, step 3, of methyl 4-((2-(3-(trifluoromethyl)benzyl)cyclopentanecarboxamido)methyl)benzoate (low $R_f$ diastereomer, 5.9 mg, 0.014 mmol) was converted into 2.6 mg (46%) of the title compound.

Example 7

4-((N-Methyl-2-(3-(trifluoromethyl)benzyl)cyclopent-1-enecarboxamido)methyl)benzoic acid

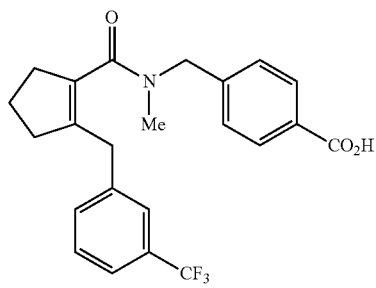 [SMILES: CN(Cc1ccc(C(=O)O)cc1)C(=O)C1=C(Cc2cccc(C(F)(F)F)c2)CCC1]

Step 1. Methyl 4-((N-methyl-2-(3-(trifluoromethyl)benzyl)cyclopent-1-enecarboxamido)methyl)benzoate A solution of lithium diisopropylamide (0.09 mL of a 2.0 M solution in THF/heptane/ethylbenzene, 0.2 mmol) was added to a −78° C. solution of methyl 4-((2-(3-(trifluoromethyl)benzyl)cyclopent-1-enecarboxamido)methyl)benzoate (see Example 4, 64.5 mg, 0.155 mmol) in THF (1.0 mL). After 20 min at −78° C., iodomethane (0.10 mL of a 2.0 M solution in t-butyl ether, 0.20 mmol) was added. The mixture was allowed to warm to room temperature and stirred for 18 h. The reaction was quenched with saturated aqueous NH$_4$Cl and extracted with CH$_2$Cl$_2$ (3×). The combined extracts were dried (MgSO$_4$), filtered and concentrated. The resulting crude residue was purified on a Teledyne-Isco Combiflash machine (12 g gold column, 20% EtOAc/hexanes→50% EtOAc/hexanes, gradient), to afford 46.6 mg (70%) of methyl 4-((N-methyl-2-(3-(trifluoromethyl)benzyl)cyclopent-1-enecarboxamido)methyl)benzoate, which appears as a 3:2 ratio of amide rotamers.

Step 2. 4-((N-Methyl-2-(3-(trifluoromethyl)benzyl)cyclopent-1-enecarboxamido)methyl)benzoic acid In accordance with the procedure of Example 3, step 3, of methyl 4-((N-methyl-2-(3-(trifluoromethyl)benzyl)cyclopent-1-enecarboxamido)methyl)benzoate (10.0 mg, 0.0232 mmol) was converted into 4.8 mg (50%) of the title compound.

Example 8

4-((2-(3,5-Dimethoxybenzyl)cyclohex-1-enecarboxamido)methyl)benzoic acid

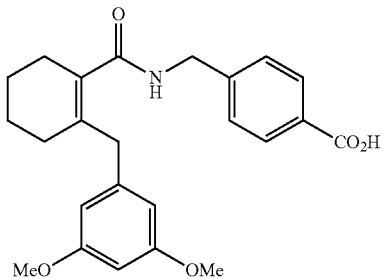 [SMILES: COc1cc(CC2=C(C(=O)NCc3ccc(C(=O)O)cc3)CCCC2)cc(OC)c1]

Step 1. Ethyl 2-(((trifluoromethyl)sulfonyl)oxy)cyclohex-1-enecarboxylate

Sodium hydride (60 wt. % in oil, 228 mg, 5.70 mmol) was added to a 0 OC solution of ethyl 2-oxocyclohexanecarboxylate (888 mg, 4.96 mmol) in THF (25 mL). After 40 min at 0° C., N-phenyl-bis(trifluoromethanesulfonimide) (2.14 g, 5.93 mmol) was added and the solution was allowed to warm to room temperature and stir overnight. The reaction mixture was quenched with saturated aqueous NaHCO$_3$ and extracted with CH$_2$Cl$_2$ (3×). The combined extracts were dried (MgSO$_4$), filtered and concentrated. The resulting crude residue was purified on a Teledyne-Isco Combiflash machine (120 g gold column, hexanes→25% EtOAc/hexanes, gradient), to afford 879 mg (59%) of ethyl 2-(((trifluoromethyl)sulfonyl)oxy)cyclohex-1-enecarboxylate.

Step 2. Ethyl 2-(3,5-dimethoxybenzyl)cyclohex-1-enecarboxylate

Palladium acetate (2.8 mg, 0.012 mmol) and SPhos (10.1 mg, 0.0239 mmol) were added to a solution of ethyl 2-(((trifluoromethyl)sulfonyl)oxy)cyclohex-1-enecarboxylate (293 mg, 0.967 mmol) in THF (1.0 mL). The reaction mixture was purged with nitrogen for 10 min and a solution of 3,5-dimethoxybenzylzinc chloride (Aldrich, 2.3 mL of a 0.5 M solution in THF, 1.2 mmol) was added drop-wise. After stirring at room temperature overnight, the reaction mixture was quenched with saturated aqueous NH$_4$Cl and extracted with EtOAc (3×). The combined extracts were dried (MgSO$_4$), filtered and concentrated. The resulting crude residue was purified on a Teledyne-Isco Combiflash machine (24 g gold column, hexanes→25% EtOAc/ hexanes, gradient), to afford 194 mg (66%) of ethyl 2-(3,5-dimethoxybenzyl)cyclohex-1-enecarboxylate.

Step 3.
2-(3,5-Dimethoxybenzyl)cyclohex-1-enecarboxylic acid

In accordance with the procedure of Example 4, step 2, ethyl 2-(3,5-dimethoxybenzyl)cyclohex-1-enecarboxylate (189 mg, 0.619 mmol) was converted into 122 mg (72%) of 2-(3,5-dimethoxybenzyl)cyclohex-1-enecarboxylic acid.

Step 4. Methyl 4-((2-(3,5-dimethoxybenzyl)cyclohex-1-enecarboxamido)methyl)benzoate In accordance with the procedure of Example 3, step 2, 2-(3,5-dimethoxybenzyl)cyclohex-1-enecarboxylic acid (120 mg, 0.435 mmol) and methyl 4-(aminomethyl)benzoate hydrochloride (90.6 mg, 0.436 mmol) were converted into 188 mg (quant.) of methyl 4-((2-(3,5-dimethoxybenzyl)cyclohex-1-enecarboxamido)methyl)benzoate.

Step 5. 4-((2-(3,5-Dimethoxybenzyl)cyclohex-1-enecarboxamido)methyl)benzoic acid In accordance with the procedure of Example 3, step 3, of methyl 4-((2-(3,5-dimethoxybenzyl)cyclohex-1-enecarboxamido)methyl)benzoate (11.4 mg, 0.0269 mmol) was converted into 5.0 mg (45%) of the title compound.

Example 9

4-((2-(3,5-Dimethoxybenzyl)cyclohexanecarboxamido)methyl)benzoic acid (from high $R_f$ ester diastereomer)

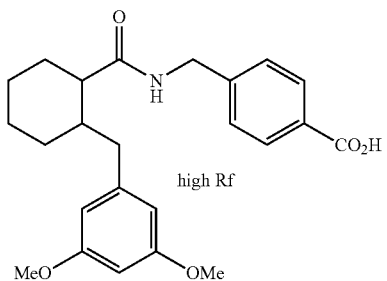 [SMILES: COc1cc(CC2CCCCC2C(=O)NCc2ccc(C(=O)O)cc2)cc(OC)c1]

high Rf

Step 1. Methyl 4-((2-(3,5-dimethoxybenzyl)cyclohexanecarboxamido)methyl)benzoate In accordance with the procedure of Example 5, step 1, methyl 4-((2-(3,5-dimethoxybenzyl)cyclohex-1-enecarboxamido)methyl)benzoate (42.9 mg, 0.101 mmol) was converted into 25.0 mg (58%) of methyl 4-((2-(3,5-dimethoxybenzyl)cyclohexanecarboxamido)methyl)benzoate (high $R_f$ diastereomer) and 14.0 mg (33%) of methyl 4-((2-(3,5-dimethoxybenzyl)cyclohexanecarboxamido)methyl)benzoate (low $R_f$ diastereomer).

Step 2. 4-((2-(3,5-Dimethoxybenzyl)cyclohexanecarboxamido)methyl)benzoic acid (from high $R_f$ ester diastereomer)

In accordance with the procedure of Example 3, step 3, methyl 4-((2-(3,5-dimethoxybenzyl)cyclohexanecarboxamido)methyl)benzoate (high $R_f$ diastereomer, 24.3 mg, 0.0571 mmol) was converted into 14.8 mg (63%) of the title compound.

Stereochemical Assignments

The two diastereomers isolated in Example 9, step 1 [methyl 4-((2-(3,5-dimethoxybenzyl)cyclohexanecarboxamido)methyl)benzoate (high $R_f$ diastereomer) and methyl 4-((2-(3,5-dimethoxybenzyl)cyclohexanecarboxamido)methyl)benzoate (low $R_f$ diastereomer)] were examined in a ROESY NMR experiment in order to determine their relative stereochemistry. Based on the enhancements observed, it was determined that the high $R_f$ diastereomer has a cis arrangement of the groups appended to the cyclohexane core, and the low $R_f$ diastereomer has a trans arrangement of the groups appended to the cyclohexane core (see FIG. 1 below). This assignment is expected to hold for all the sets of diastereomers described herein, however a skilled person can determine the relative and/or absolute stereochemistry by using routine techniques known in the art (e.g. ROESY NMR).

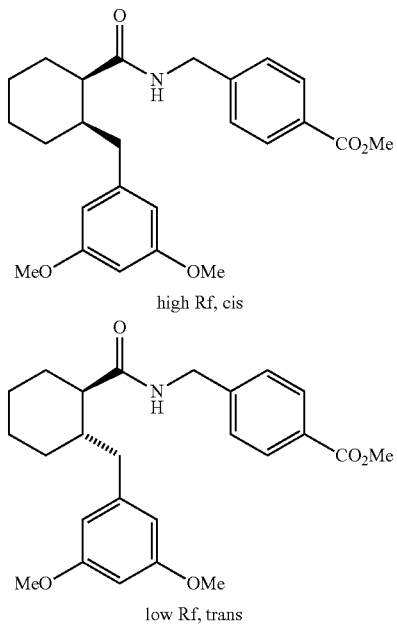

Example 10

4-((2-(3,5-Dimethoxybenzyl)cyclohexanecarboxamido)methyl)benzoic acid (from low $R_f$ ester diastereomer, see Example 9)

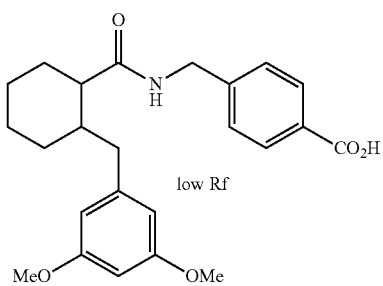

low Rf

In accordance with the procedure of Example 3, step 3, methyl 4-((2-(3,5-dimethoxybenzyl)cyclohexanecarboxamido)methyl)benzoate (low R$_f$ diastereomer, 13.7 mg, 0.0322 mmol) was converted into 5.8 mg (44%) of the title compound.

Example 11

4-((2-(3,5-Dimethoxybenzyl)cyclohept-1-enecarboxamido)methyl)benzoic acid

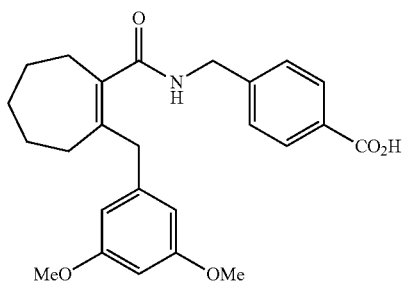 [SMILES: COc1cc(CC2=C(C(=O)NCc3ccc(C(=O)O)cc3)CCCCC2)cc(OC)c1]

Step 1. Methyl 2-(((trifluoromethyl)sulfonyl)oxy)cyclohept-1-enecarboxylate In accordance with the procedure of Example 8, step 1, methyl 2-oxocycloheptanecarboxylate (797 mg, 4.64 mmol) was converted into 621 mg (44%) of methyl 2-(((trifluoromethyl)sulfonyl)oxy)cyclohept-1-enecarboxylate after purification on a Teledyne-Isco Combiflash machine (80 g gold column, hexanes→25% EtOAc/hexanes, gradient).

Step 2. Methyl 2-(3,5-dimethoxybenzyl)cyclohept-1-enecarboxylate

In accordance with the procedure of Example 8, step 2, methyl 2-(((trifluoromethyl)sulfonyl)oxy)cyclohept-1-enecarboxylate (256 mg, 0.846 mmol) was converted into 167 mg (65%) of methyl 2-(3,5-dimethoxybenzyl)cyclohept-1-enecarboxylate.

Step 3. 2-(3,5-Dimethoxybenzyl)cyclohept-1-enecarboxylic acid

In accordance with the procedure of Example 4, step 2, methyl 2-(3,5-dimethoxybenzyl)cyclohept-1-enecarboxylate (167 mg, 0.549 mmol) was converted into 137 mg (86%) of 2-(3,5-dimethoxybenzyl)cyclohept-1-enecarboxylic acid.

Step 4. Methyl 4-((2-(3,5-dimethoxybenzyl)cyclohept-1-enecarboxamido)methyl)benzoate In accordance with the procedure of Example 3, step 2, 2-(3,5-dimethoxybenzyl)cyclohept-1-enecarboxylic acid (124 mg, 0.427 mmol) and methyl 4-(aminomethyl)benzoate hydrochloride (89.2 mg, 0.429 mmol) were converted into 189 mg (quant.) of methyl 4-((2-(3,5-dimethoxybenzyl)cyclohept-1-enecarboxamido)methyl)benzoate.

Step 5. 4-((2-(3,5-Dimethoxybenzyl)cyclohept-1-enecarboxamido)methyl)benzoic acid In accordance with the procedure of Example 3, step 3, of methyl 4-((2-(3,5-dimethoxybenzyl)cyclohept-1-enecarboxamido)methyl)benzoate (8.6 mg, 0.020 mmol) was converted into 2.3 mg (28%) of the title compound.

Example 12

4-((2-(3,5-Dimethoxybenzyl)cycloheptanecarboxamido)methyl)benzoic acid (from high R$_f$ ester diastereomer, see Example 11)

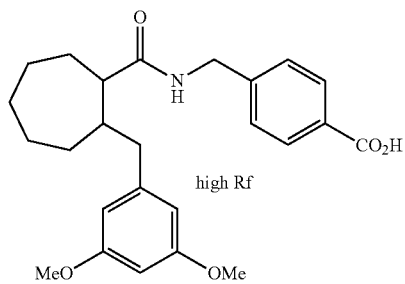 [SMILES: COc1cc(CC2CCCCCC2C(=O)NCc2ccc(C(=O)O)cc2)cc(OC)c1]

high Rf

Step 1. Methyl 4-((2-(3,5-dimethoxybenzyl)cycloheptanecarboxamido) methyl)benzoate In accordance with the procedure of Example 5, step 1, methyl 4-((2-(3,5-dimethoxybenzyl)cyclohept-1-enecarboxamido)methyl)benzoate (41.6 mg, 0.0951 mmol) was converted into 25.0 mg (62%) of methyl 4-((2-(3,5-dimethoxybenzyl)cycloheptanecarboxamido)methyl)benzoate (high R$_f$ diastereomer) and 9.6 mg (23%) of methyl 4-((2-(3,5-dimethoxybenzyl)cycloheptanecarboxamido)methyl)benzoate (low R$_f$ diastereomer).

Step 2. 4-((2-(3,5-Dimethoxybenzyl)cycloheptanecarboxamido)methyl)benzoic acid (from high R$_f$ ester diastereomer)

In accordance with the procedure of Example 3, step 3, methyl 4-((2-(3,5-dimethoxybenzyl)cycloheptanecarboxamido)methyl)benzoate (high R$_f$ diastereomer, 23.8 mg, 0.0541 mmol) was converted into 15.3 mg (67%) of the title compound.

Example 13

4-((2-(3,5-Dimethoxybenzyl)cycloheptanecarboxamido)methyl)benzoic acid (from low R$_f$ ester diastereomer, see Example 12)

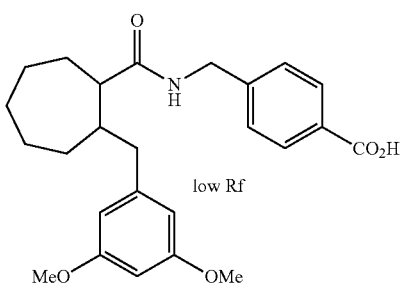 [SMILES: COc1cc(CC2CCCCCC2C(=O)NCc2ccc(C(=O)O)cc2)cc(OC)c1]

low Rf

In accordance with the procedure of Example 3, step 3, methyl 4-((2-(3,5-dimethoxybenzyl)cycloheptanecarboxamido)methyl)benzoate (low R_f diastereomer, 9.5 mg, 0.022 mmol) was converted into 3.3 mg (36%) of the title compound.

Example 14

4-((2-(2,3-Dimethoxybenzyl)cyclohex-1-enecarboxamido)methyl)benzoic acid

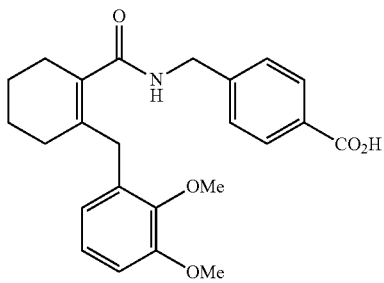 [SMILES: COc1cccc(CC2=C(C(=O)NCc3ccc(C(=O)O)cc3)CCCC2)c1OC]

Step 1. Ethyl 2-(2,3-dimethoxybenzyl)cyclohex-1-enecarboxylate

In accordance with the procedure of Example 8, step 2, ethyl 2-(((trifluoromethyl)sulfonyl)oxy)cyclohex-1-enecarboxylate (193 mg, 0.64 mmol) and 2,3-dimethoxybenzylzinc chloride (Rieke Metals, 1.5 mL of a 0.5 M solution in THF, 0.75 mmol) were converted into 123 mg (63%) of ethyl 2-(2,3-dimethoxybenzyl)cyclohex-1-enecarboxylate after purification on a Teledyne-Isco Combiflash machine (12 g gold column, hexanes→25% EtOAc/hexanes, gradient).

Step 2. 2-(2,3-Dimethoxybenzyl)cyclohex-1-enecarboxylic acid

In accordance with the procedure of Example 4, step 2, ethyl 2-(2,3-dimethoxybenzyl)cyclohex-1-enecarboxylate (120 mg, 0.395 mmol) was converted into 66.6 mg (61%) of 2-(2,3-dimethoxybenzyl)cyclohex-1-enecarboxylic acid.

Step 3. Methyl 4-((2-(2,3-dimethoxybenzyl)cyclohex-1-enecarboxamido)methyl)benzoate In accordance with the procedure of Example 3, step 2, 2-(2,3-dimethoxybenzyl)cyclohex-1-enecarboxylic acid (64.8 mg, 0.234 mmol) and methyl 4-(aminomethyl)benzoate hydrochloride (49 mg, 0.235 mmol) were converted into 103 mg (quant.) of methyl 4-((2-(2,3-dimethoxybenzyl) cyclohex-1-enecarboxamido)methyl)benzoate.

Step 4. 4-((2-(2,3-dimethoxybenzyl)cyclohex-1-enecarboxamido)methyl)benzoic acid In accordance with the procedure of Example 3, step 3, of methyl 4-((2-(2,3-Dimethoxybenzyl)cyclohex-1-enecarboxamido)methyl)benzoate (12.0 mg, 0.0283 mmol) was converted into 5.4 mg (47%) of the title compound.

Example 15

4-((2-(2,3-Dimethoxybenzyl)cyclohexanecarboxamido)methyl)benzoic acid (from high R_f ester diastereomer)

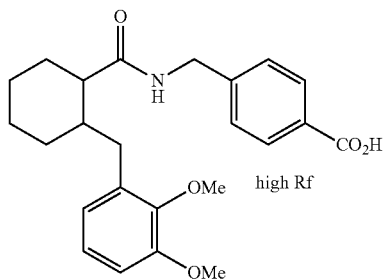 [SMILES: COc1cccc(CC2CCCCC2C(=O)NCc2ccc(C(=O)O)cc2)c1OC]

Step 1. Methyl 4-((2-(2,3-dimethoxybenzyl)cyclohexanecarboxamido)methyl)benzoate In accordance with the procedure of Example 5, step 1, methyl 4-((2-(2,3-dimethoxybenzyl)cyclohex-1-enecarboxamido)methyl)benzoate (38.8 mg, 0.0916 mmol) was converted into 20.1 mg (52%) of methyl 4-((2-(2,3-dimethoxybenzyl)cyclohexanecarboxamido)methyl)benzoate (high R_f diastereomer) and 15.0 mg (39%) of methyl 4-((2-(2,3-dimethoxybenzyl)cyclohexanecarboxamido)methyl)benzoate (low R_f diastereomer).

Step 2. 4-((2-(2,3-Dimethoxybenzyl)cyclohexanecarboxamido)methyl)benzoic acid (from high R_f ester diastereomer)

In accordance with the procedure of Example 3, step 3, methyl 4-((2-(2,3-dimethoxybenzyl)cyclohexanecarboxamido)methyl)benzoate (high R_f diastereomer, 20.1 mg, 0.0472 mmol) was converted into 11.2 mg (58%) of the title compound.

Example 16

4-((2-(2,3-Dimethoxybenzyl)cyclohexanecarboxamido)methyl)benzoic acid (from low R_f ester diastereomer, see Example 14)

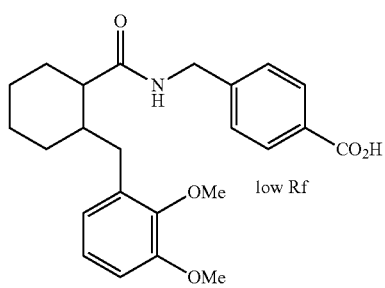

In accordance with the procedure of Example 3, step 3, methyl 4-((2-(2,3-dimethoxybenzyl)cyclohexanecarboxamido)methyl)benzoate (low $R_f$ diastereomer, 15.0 mg, 0.0353 mmol) was converted into 6.4 mg (44%) of the title compound.

Example 17

4-((2-(2,5-Dimethoxybenzyl)cyclohex-1-enecarboxamido)methyl)benzoic acid

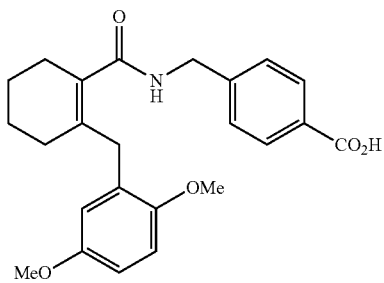 [SMILES: COc1ccc(OC)c(CC2=C(C(=O)NCc3ccc(C(=O)O)cc3)CCCC2)c1]

Step 1. Ethyl 2-(2,5-dimethoxybenzyl)cyclohex-1-enecarboxylate

In accordance with the procedure of Example 8, step 2, ethyl 2-(((trifluoromethyl)sulfonyl)oxy)cyclohex-1-enecarboxylate (193 mg, 0.637 mmol) and 2,5-dimethoxybenzylzinc chloride (Rieke Metals, 1.5 mL of a 0.5 M solution in THF, 0.75 mmol) were converted into 142 mg (73%) of ethyl 2-(2,5-dimethoxybenzyl)cyclohex-1-enecarboxylate after purification on a Teledyne-Isco Combiflash machine (12 g gold column, hexanes→25% EtOAc/hexanes, gradient).

Step 2. 2-(2,5-Dimethoxybenzyl)cyclohex-1-enecarboxylic acid

In accordance with the procedure of Example 4, step 2, ethyl 2-(2,5-dimethoxybenzyl)cyclohex-1-enecarboxylate (137 mg, 0.450 mmol) was converted into 73.5 mg (59%) of 2-(2,5-dimethoxybenzyl)cyclohex-1-enecarboxylic acid.

Step 3. Methyl 4-((2-(2,5-dimethoxybenzyl)cyclohex-1-enecarboxamido) methyl)benzoate In accordance with the procedure of Example 3, step 2, 2-(2,5-dimethoxybenzyl)cyclohex-1-enecarboxylic acid (71.9 mg, 0.260 mmol) and methyl 4-(aminomethyl)benzoate hydrochloride (54.0 mg, 0.260 mmol) were converted into 110 mg (quant.) of methyl 4-((2-(2,5-dimethoxybenzyl)cyclohex-1-enecarboxamido)methyl)benzoate.

Step 4. 4-((2-(2,5-Dimethoxybenzyl)cyclohex-1-enecarboxamido)methyl)benzoic acid In accordance with the procedure of Example 3, step 3, of methyl 4-((2-(2,5-dimethoxybenzyl)cyclohex-1-enecarboxamido)methyl)benzoate (10.3 mg, 0.0243 mmol) was converted into 5.8 mg (58%) of the title compound.

Example 18

4-((2-(2,5-Dimethoxybenzyl)cyclohexanecarboxamido)methyl)benzoic acid (from high $R_f$ ester diastereomer)

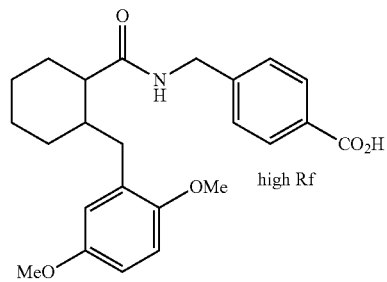 [SMILES: COc1ccc(OC)c(CC2CCCCC2C(=O)NCc2ccc(C(=O)O)cc2)c1]

Step 1. Methyl 4-((2-(2,5-dimethoxybenzyl)cyclohexanecarboxamido) methyl)benzoate In accordance with the procedure of Example 5, step 1, methyl 4-((2-(2,5-dimethoxybenzyl)cyclohex-1-enecarboxamido)methyl)benzoate (40.3 mg, 0.0952 mmol) was converted into 21.0 mg (52%) of methyl 4-((2-(2,5-dimethoxybenzyl)cyclohexanecarboxamido)methyl)benzoate (high $R_f$ diastereomer) and 13.8 mg (34%) of methyl 4-((2-(2,5-dimethoxybenzyl)cyclohexanecarboxamido)methyl)benzoate (low $R_f$ diastereomer).

Step 2. 4-((2-(2,5-Dimethoxybenzyl)cyclohexanecarboxamido)methyl)benzoic acid (from high $R_f$ ester diastereomer)

In accordance with the procedure of Example 3, step 3, methyl 4-((2-(2,5-dimethoxybenzyl)cyclohexanecarboxamido)methyl)benzoate (high $R_f$ diastereomer, 20.0 mg, 0.0470 mmol) was converted into 6.7 mg (35%) of the title compound.

Example 19

4-((2-(2,5-Dimethoxybenzyl)cyclohexanecarboxamido)methyl)benzoic acid (from low $R_f$ ester diastereomer, see Example 18)

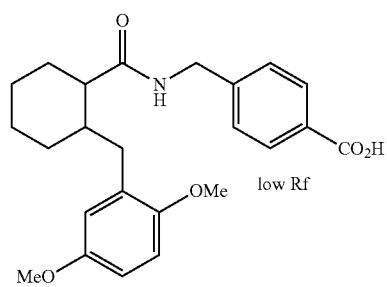 [SMILES: COc1ccc(OC)c(CC2CCCCC2C(=O)NCc2ccc(C(=O)O)cc2)c1]

In accordance with the procedure of Example 3, step 3, methyl 4-((2-(2,5-dimethoxybenzyl)cyclohexanecarboxamido)methyl)benzoate (low $R_f$ diastereomer, 13.8 mg, 0.0324 mmol) was converted into 5.4 mg (41%) of the title compound.

Example 20

4-((2-(3,5-Dimethoxybenzyl)cyclooct-1-enecarboxamido)methyl)benzoic acid

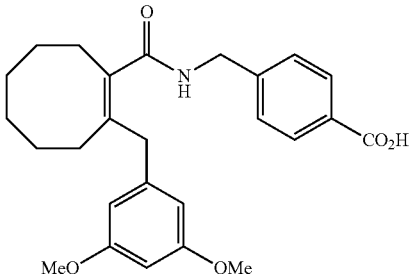 [SMILES: COc1cc(C/C2=C(\C(=O)NCc3ccc(C(=O)O)cc3)CCCCCC2)cc(OC)c1]

Step 1. Ethyl 2-(((trifluoromethyl)sulfonyl)oxy)cyclooct-1-enecarboxylate

In accordance with the procedure of Example 8, step 1, ethyl 2-oxocyclooctanecarboxylate (Aldrich, 829 mg, 4.06 mmol) was converted into 497 mg (37%) of ethyl 2-(((trifluoromethyl)sulfonyl)oxy)cyclooct-1-enecarboxylate.

Step 2. Ethyl 2-(3,5-dimethoxybenzyl)cyclooct-1-enecarboxylate

In accordance with the procedure of Example 8, step 2, ethyl 2-(((trifluoromethyl)sulfonyl)oxy)cyclohex-1-enecarboxylate (224 mg, 0.679 mmol) and of 3,5-dimethoxybenzylzinc chloride (Aldrich, 1.6 mL of a 0.5 M solution in THF, 0.80 mmol) were converted into 98.4 mg (44%) of ethyl 2-(3,5-dimethoxybenzyl)cyclooct-1-enecarboxylate.

Step 3. 2-(3,5-Dimethoxybenzyl)cyclooct-1-enecarboxylic acid

In accordance with the procedure of Example 4, step 2, ethyl 2-(3,5-dimethoxybenzyl)cyclooct-1-enecarboxylate (94.8 mg, 0.285 mmol), with stirring at 80° C., was converted into 20.7 mg (24%) of 2-(3,5-dimethoxybenzyl)cyclooct-1-enecarboxylic acid, along with a 60.0 mg (63%) of starting ester.

Step 4. Methyl 4-((2-(3,5-dimethoxybenzyl)cyclooct-1-enecarboxamido)methyl)benzoate In accordance with the procedure of Example 3, step 2, 2-(3,5-dimethoxybenzyl)cyclooct-1-enecarboxylic acid (62.3 mg, 0.205 mmol) and methyl 4-(aminomethyl)benzoate hydrochloride (42.7 mg, 0.205 mmol) were converted into 85.8 mg (93%) of methyl 4-((2-(3,5-dimethoxybenzyl)cyclooct-1-enecarboxamido)methyl)benzoate.

Step 5. 4-((2-(3,5-Dimethoxybenzyl)cyclooct-1-enecarboxamido)methyl)benzoic acid In accordance with the procedure of Example 3, step 3, of methyl 4-((2-(3,5-dimethoxybenzyl)cyclooct-1-enecarboxamido)methyl)benzoate (11.1 mg, 0.0246 mmol) was converted into 5.7 mg (53%) of the title compound.

Example 21

4-((2-(3,4-Dimethoxybenzyl)cyclohex-1-enecarboxamido)methyl)benzoic acid

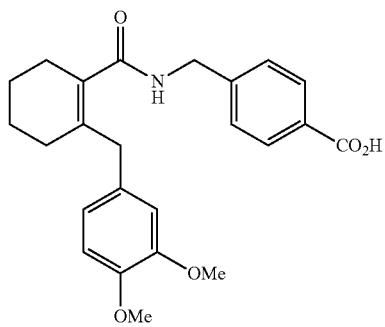 [SMILES: COc1ccc(CC2=C(C(=O)NCc3ccc(C(=O)O)cc3)CCCC2)cc1OC]

Step 1. Ethyl 2-(3,4-dimethoxybenzyl)cyclohex-1-enecarboxylate

In accordance with the procedure of Example 8, step 2, ethyl 2-(((trifluoromethyl)sulfonyl)oxy)cyclohex-1-enecarboxylate (198 mg, 0.654 mmol) and 3,4-dimethoxybenzylzinc chloride (Rieke Metals, 1.6 mL of a 0.5 M solution in THF, 0.80 mmol) were converted into 122 mg (61%) of ethyl 2-(3,4-dimethoxybenzyl)cyclohex-1-enecarboxylate after purification on a Teledyne-Isco Combiflash machine (12 g gold column, hexanes→20% EtOAc/hexanes, gradient).

Step 2. 2-(3,4-Dimethoxybenzyl)cyclohex-1-enecarboxylic acid

In accordance with the procedure of Example 4, step 2, ethyl 2-(3,4-dimethoxybenzyl)cyclohex-1-enecarboxylate (120 mg, 0.393 mmol) was converted into 92 mg (85%) of 2-(3,4-dimethoxybenzyl)cyclohex-1-enecarboxylic acid.

Step 3. Methyl 4-((2-(3,4-dimethoxybenzyl)cyclohex-1-enecarboxamido)methyl)benzoate In accordance with the procedure of Example 3, step 2, 2-(3,4-dimethoxybenzyl)cyclohex-1-enecarboxylic acid (92 mg, 0.33 mmol) and methyl 4-(aminomethyl)benzoate hydrochloride (69 mg, 0.33 mmol) were converted into 131 mg (93%) of methyl 4-((2-(3,4-dimethoxybenzyl)cyclohex-1-enecarboxamido)methyl)benzoate.

Step 4. 4-((2-(3,4-Dimethoxybenzyl)cyclohex-1-enecarboxamido)methyl)benzoic acid In accordance with the procedure of Example 3, step 3, of methyl 4-((2-(3,4-dimethoxybenzyl)cyclohex-1-enecarboxamido)methyl)benzoate (11.2 mg, 0.0264 mmol) was converted into 4.3 mg (40%) of the title compound.

Example 22

4-((2-(3,4-Dimethoxybenzyl)cyclohexanecarboxamido)methyl)benzoic acid (from high R_f ester diastereomer)

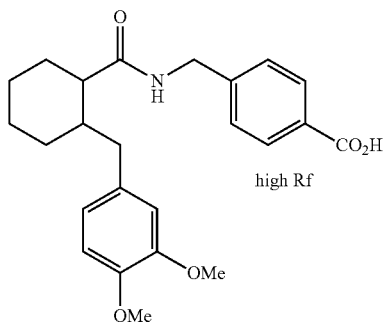 [SMILES: COc1ccc(CC2CCCCC2C(=O)NCc2ccc(C(=O)O)cc2)cc1OC]

high Rf

Step 1. Methyl 4-((2-(3,4-dimethoxybenzyl)cyclohexanecarboxamido)methyl)benzoate In accordance with the procedure of Example 5, step 1, methyl 4-((2-(3,4-dimethoxybenzyl)cyclohex-1-enecarboxamido)methyl)benzoate (40 mg, 0.095 mmol) was converted into 27.5 mg (68%) of methyl 4-((2-(3,4-dimethoxybenzyl)cyclohexanecarboxamido)methyl)benzoate (high $R_f$ diastereomer) and 10.9 mg (27%) of methyl 4-((2-(3,4-dimethoxybenzyl)cyclohexanecarboxamido)methyl)benzoate (low $R_f$ diastereomer).

Step 2. 4-((2-(3,4-Dimethoxybenzyl)cyclohexanecarboxamido)methyl)benzoic acid (from high $R_f$ ester diastereomer)

In accordance with the procedure of Example 3, step 3, methyl 4-((2-(3,4-dimethoxybenzyl)cyclohexanecarboxamido)methyl)benzoate (high $R_f$ diastereomer, 27.5 mg, 0.0646 mmol) was converted into 16.1 mg (61%) of the title compound.

Example 23

4-((2-(3,4-Dimethoxybenzyl)cyclohexanecarboxamido)methyl)benzoic acid (from low $R_f$ ester diastereomer, see Example 22)

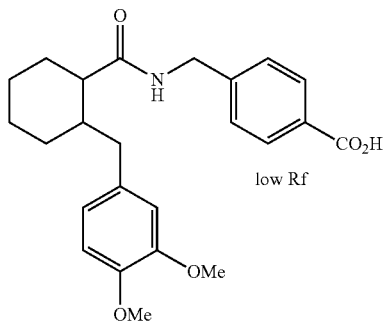 [SMILES: COc1ccc(CC2CCCCC2C(=O)NCc2ccc(C(=O)O)cc2)cc1OC]

low Rf

In accordance with the procedure of Example 3, step 3, methyl 4-((2-(3,4-dimethoxybenzyl)cyclohexanecarboxamido)methyl)benzoate (low $R_f$ diastereomer, 10.4 mg, 0.0244 mmol) was converted into 4.1 mg (41%) of the title compound.

Example 24

4-((2-(2-Chlorobenzyl)cyclohex-1-enecarboxamido)methyl)benzoic acid

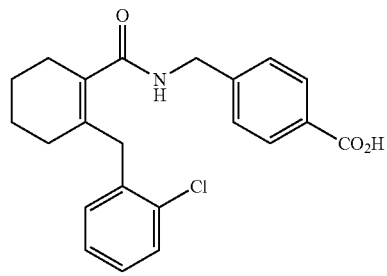 [SMILES: O=C(NCc1ccc(C(=O)O)cc1)C1=C(Cc2ccccc2Cl)CCCC1]

Step 1. Ethyl 2-(2-chlorobenzyl)cyclohex-1-enecarboxylate

In accordance with the procedure of Example 8, step 2, ethyl 2-(((trifluoromethyl)sulfonyl)oxy)cyclohex-1-enecarboxylate (300 mg, 0.993 mmol) and 2-chlorobenzylzinc(II) chloride (Aldrich, 2.4 mL of a 0.5 M solution in THF, 1.2 mmol) were converted into 144 mg (52%) of ethyl 2-(2-chlorobenzyl)cyclohex-1-enecarboxylate after purification on a Teledyne-Isco Combiflash machine (24 g gold column, hexanes→15% EtOAc/hexanes, gradient).

Step 2. 2-(2-Chlorobenzyl)cyclohex-1-enecarboxylic acid

In accordance with the procedure of Example 4, step 2, ethyl 2-(2-chlorobenzyl)cyclohex-1-enecarboxylate (55 mg, 0.197 mmol) was converted into 42.4 mg (86%) of 2-(2-chlorobenzyl)cyclohex-1-enecarboxylic acid after purification on a Teledyne-Isco Combiflash machine (4 g gold column, hexanes→35% EtOAc/hexanes, gradient).

Step 3. Methyl 4-((2-(2-chlorobenzyl)cyclohex-1-enecarboxamido)methyl)benzoate In accordance with the procedure of Example 3, step 2, 2-(2-chlorobenzyl)cyclohex-1-enecarboxylic acid (41 mg, 0.16 mmol) and methyl 4-(aminomethyl)benzoate hydrochloride (34 mg, 0.16 mmol) were converted into 64 mg (99%) of methyl 4-((2-(2-chlorobenzyl)cyclohex-1-enecarboxamido)methyl)benzoate.

Step 4. 4-((2-(2-Chlorobenzyl)cyclohex-1-enecarboxamido)methyl)benzoic acid

In accordance with the procedure of Example 3, step 3, methyl 4-((2-(2-chlorobenzyl)cyclohex-1-enecarboxamido)methyl)benzoate (9.4 mg, 0.0236 mmol) was converted into 4.0 mg (44%) of the title compound.

Example 25

4-((2-Benzylcyclohexanecarboxamido)methyl)benzoic acid (from high $R_f$ ester diastereomer)

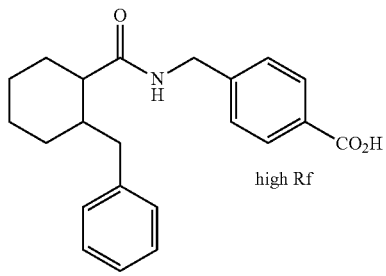 [SMILES: O=C(O)c1ccc(CNC(=O)C2CCCCC2Cc2ccccc2)cc1]

high Rf

Step 1. Methyl 4-((2-benzylcyclohexanecarboxamido)methyl)benzoate

In accordance with the procedure of Example 5, step 1, methyl 4-((2-(2-chlorobenzyl)cyclohex-1-enecarboxamido)methyl)benzoate (47 mg, 0.12 mmol) was converted into 26.6 mg (62%) of methyl 4-((2-benzylcyclohexanecarboxamido)methyl)benzoate (high $R_f$ diastereomer) and 9.3 mg (22%) of methyl 4-((2-benzylcyclohexanecarboxamido)methyl)benzoate (low $R_f$ diastereomer). No product containing the starting chloro substituent was isolated.

Step 2. 4-((2-Benzylcyclohexanecarboxamido)methyl)benzoic acid (from high $R_f$ ester diastereomer)

In accordance with the procedure of Example 3, step 3, methyl 4-((2-benzylcyclohexanecarboxamido)methyl)benzoate (high $R_f$ diastereomer, 26.6 mg, 0.0728 mmol) was converted into 18.7 mg (73%) of the title compound.

Example 26

4-((2-Benzylcyclohexanecarboxamido)methyl)benzoic acid (from low $R_f$ ester diastereomer)

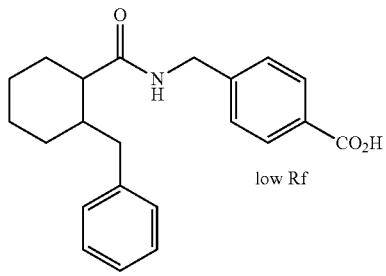 [SMILES: O=C(O)c1ccc(CNC(=O)C2CCCCC2Cc2ccccc2)cc1]

low Rf

In accordance with the procedure of Example 3, step 3, methyl 4-((2-benzylcyclohexanecarboxamido)methyl)benzoate (low $R_f$ diastereomer, 9.3 mg, 0.0254 mmol) was converted into 4.5 mg (50%) of the title compound.

Example 27

4-((2-(3-Methoxybenzyl)cyclohex-1-enecarboxamido)methyl)benzoic acid

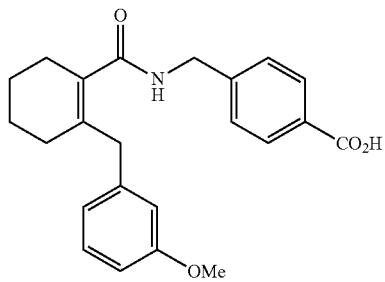 [SMILES: COc1cccc(CC2=C(C(=O)NCc3ccc(C(=O)O)cc3)CCCC2)c1]

Step 1. Ethyl 2-(3-methoxybenzyl)cyclohex-1-enecarboxylate

In accordance with the procedure of Example 8, step 2, ethyl 2-((((trifluoromethyl)sulfonyl)oxy)cyclohex-1-enecarboxylate (190 mg, 0.628 mmol) and 3-methoxybenzylzinc (II) chloride (Rieke Metals, 1.5 mL of a 0.5 M solution in THF, 0.75 mmol) were converted into 152 mg of ethyl 2-(3-methoxybenzyl)cyclohex-1-enecarboxylate contaminated with the triflate starting material after purification on a Teledyne-Isco Combiflash machine (12 g gold column, hexanes→15% EtOAc/hexanes, gradient). The estimated yield of the desired product, accounting for impurity based on 1H-NMR analysis, is approximately 115 mg (~67%).

Step 2. 2-(3-Methoxybenzyl)cyclohex-1-enecarboxylic acid

In accordance with the procedure of Example 4, step 2, ethyl 2-(3-methoxybenzyl)cyclohex-1-enecarboxylate (152 mg of the impure material from step 1, ~0.42 mmol) was converted into 86.4 mg (~84%) of 2-(3-methoxybenzyl)cyclohex-1-enecarboxylic acid after purification on a Teledyne-Isco Combiflash machine (12 g gold column, hexanes→35% EtOAc/hexanes, gradient).

Step 3. Methyl 4-((2-(3-methoxybenzyl)cyclohex-1-enecarboxamido)methyl)benzoate In accordance with the procedure of Example 3, step 2, 2-(3-methoxybenzyl)cyclohex-1-enecarboxylic acid (83 mg, 0.34 mmol) and methyl 4-(aminomethyl)benzoate hydrochloride (70 mg, 0.34 mmol) were converted into 136 mg (quant.) of methyl 4-((2-(3-methoxybenzyl)cyclohex-1-enecarboxamido)methyl)benzoate.

Step 4. 4-((2-(3-Methoxybenzyl)cyclohex-1-enecarboxamido)methyl)benzoic acid In accordance with the procedure of Example 3, step 3, methyl 4-((2-(3-methoxybenzyl)cyclohex-1-enecarboxamido)methyl)benzoate (8.3 mg, 0.021 mmol) was converted into 2.9 mg (36%) of the title compound.

Example 28

4-((2-(3-Methoxybenzyl)cyclohexanecarboxamido)methyl)benzoic acid (from high R*f* ester diastereomer)

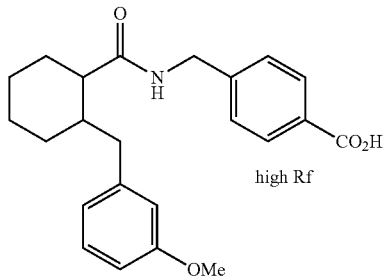 [SMILES: COc1cccc(CC2CCCCC2C(=O)NCc2ccc(C(=O)O)cc2)c1]

high Rf

Step 1. Methyl 4-((2-(3-methoxybenzyl)cyclohexanecarboxamido)methyl)benzoate In accordance with the procedure of Example 5, step 1, methyl 4-((2-(3-methoxybenzyl)cyclohex-1-enecarboxamido)methyl)benzoate (37 mg, 0.094 mmol) was converted into 15 mg (40%) of methyl 4-((2-(3-methoxybenzyl)cyclohexanecarboxamido)methyl)benzoate (high R*f* diastereomer) and 7.2 mg (19%) of methyl 4-((2-(3-methoxybenzyl)cyclohexanecarboxamido)methyl)benzoate (low R*f* diastereomer).

Step 2. 4-((2-(3-Methoxybenzyl)cyclohexanecarboxamido)methyl)benzoic acid (from high R*f* ester diastereomer)

In accordance with the procedure of Example 3, step 3, methyl 4-((2-(3-methoxybenzyl)cyclohexanecarboxamido)methyl)benzoate (high R*f* diastereomer, 15 mg, 0.038 mmol) was converted into 8.2 mg (57%) of the title compound.

Example 29

4-((2-(3-Methoxybenzyl)cyclohexanecarboxamido)methyl)benzoic acid (from low R*f* ester diastereomer)

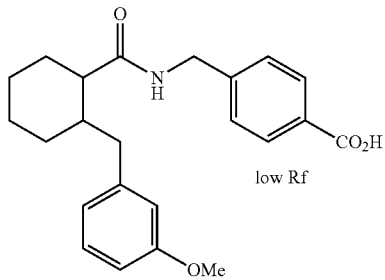 [SMILES: COc1cccc(CC2CCCCC2C(=O)NCc2ccc(C(=O)O)cc2)c1]

low Rf

In accordance with the procedure of Example 3, step 3, methyl 4-((2-(3-methoxybenzyl)cyclohexanecarboxamido)methyl)benzoate (low R*f* diastereomer, 7.2 mg, 0.018 mmol) was converted into 2.9 mg (42%) of the title compound.

Example 30

4-((2-(2-Methoxybenzyl)cyclohex-1-enecarboxamido)methyl)benzoic acid

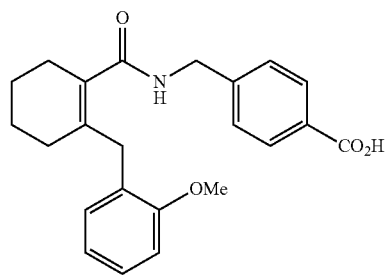 [SMILES: COc1ccccc1CC1=C(C(=O)NCc2ccc(C(=O)O)cc2)CCCC1]

Step 1. Ethyl 2-(2-methoxybenzyl)cyclohex-1-enecarboxylate

In accordance with the procedure of Example 8, step 2, ethyl 2-(((trifluoromethyl)sulfonyl)oxy)cyclohex-1-enecarboxylate (190 mg, 0.628 mmol) and 2-methoxybenzylzinc (II) chloride (Rieke Metals, 1.5 mL of a 0.5 M solution in THF, 0.75 mmol) were converted into 160 mg of ethyl 2-(2-methoxybenzyl)cyclohex-1-enecarboxylate contaminated with the triflate starting material after purification on a Teledyne-Isco Combiflash machine (12 g gold column, hexanes→15% EtOAc/hexanes, gradient). The estimated yield of the desired product, accounting for impurity based on 1H-NMR analysis, is approximately 119 mg (~69%).

Step 2. 2-(2-Methoxybenzyl)cyclohex-1-enecarboxylic acid

In accordance with the procedure of Example 4, step 2, ethyl 2-(2-methoxybenzyl)cyclohex-1-enecarboxylate (160 mg of the impure material from step 1, ~0.42 mmol) was converted into 84 mg (~81%) of 2-(2-methoxybenzyl)cyclohex-1-enecarboxylic acid after purification on a Teledyne-Isco Combiflash machine (12 g gold column, hexanes→35% EtOAc/hexanes, gradient).

Step 3. Methyl 4-((2-(2-methoxybenzyl)cyclohex-1-enecarboxamido)methyl)benzoate In accordance with the procedure of Example 3, step 2, 2-(2-methoxybenzyl)cyclohex-1-enecarboxylic acid (80 mg, 0.33 mmol) and methyl 4-(aminomethyl)benzoate hydrochloride (68 mg, 0.33 mmol) were converted into 121 mg (94%) of methyl 4-((2-(2-methoxybenzyl)cyclohex-1-enecarboxamido)methyl)benzoate.

Step 4. 4-((2-(2-Methoxybenzyl)cyclohex-1-enecarboxamido)methyl)benzoic acid In accordance with the procedure of Example 3, step 3, methyl 4-((2-(2-methoxybenzyl)cyclohex-1-enecarboxamido)methyl)benzoate (10.3 mg, 0.0262 mmol) was converted into 4.5 mg (45%) of the title compound.

Example 31

4-((2-(2-Methoxybenzyl)cyclohexanecarboxamido)methyl)benzoic acid (from high R_f ester diastereomer)

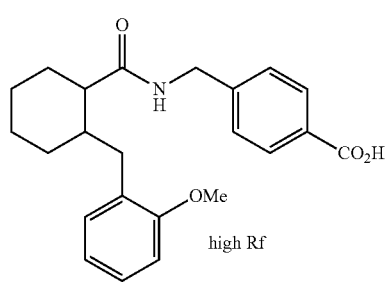 [SMILES: COc1ccccc1CC1CCCCC1C(=O)NCc1ccc(C(=O)O)cc1]

high Rf

Step 1. Methyl 4-((2-(2-methoxybenzyl)cyclohexanecarboxamido)methyl)benzoate In accordance with the procedure of Example 5, step 1, methyl 4-((2-(2-methoxybenzyl)cyclohex-1-enecarboxamido)methyl)benzoate (40 mg, 0.10 mmol) was converted into 18.8 mg (47%) of methyl 4-((2-(2-methoxybenzyl)cyclohexanecarboxamido)methyl)benzoate (high R_f diastereomer) and 13.5 mg (34%) of methyl 4-((2-(2-methoxybenzyl)cyclohexanecarboxamido)methyl)benzoate (low R_f diastereomer).

Step 2. 4-((2-(2-Methoxybenzyl)cyclohexanecarboxamido)methyl)benzoic acid (from high R_f ester diastereomer)

In accordance with the procedure of Example 3, step 3, methyl 4-((2-(2-methoxybenzyl)cyclohexanecarboxamido)methyl)benzoate (high R_f diastereomer, 18.8 mg, 0.0475 mmol) was converted into 8.9 mg (49%) of the title compound.

Example 32

4-((2-(2-Methoxybenzyl)cyclohexanecarboxamido)methyl)benzoic acid (from low R_f ester diastereomer)

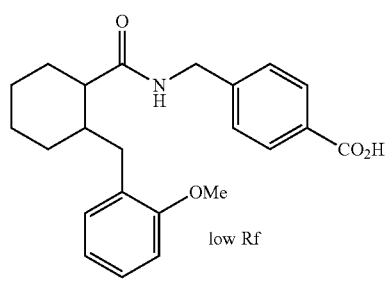 [SMILES: COc1ccccc1CC1CCCCC1C(=O)NCc1ccc(C(=O)O)cc1]

low Rf

In accordance with the procedure of Example 3, step 3, methyl 4-((2-(2-methoxybenzyl)cyclohexanecarboxamido)methyl)benzoate (low R_f diastereomer, 13.5 mg, 0.0341 mmol) was converted into 7.2 mg (55%) of the title compound.

Example 33

4-((2-(4-Methoxybenzyl)cyclohex-1-enecarboxamido)methyl)benzoic acid

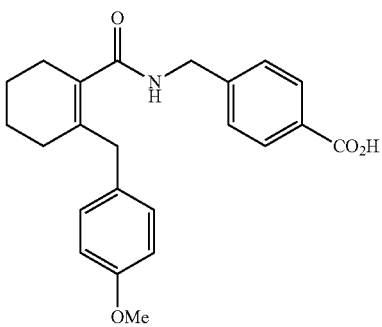 [SMILES: COc1ccc(CC2=C(C(=O)NCc3ccc(C(=O)O)cc3)CCCC2)cc1]

Step 1. Ethyl 2-(4-methoxybenzyl)cyclohex-1-enecarboxylate

In accordance with the procedure of Example 8, step 2, ethyl 2-(((trifluoromethyl)sulfonyl)oxy)cyclohex-1-enecarboxylate (199 mg, 0.659 mmol) and 4-methoxybenzylzinc(II) chloride (Rieke Metals, 1.6 mL of a 0.5 M solution in THF, 0.80 mmol) were converted into 156 mg of ethyl 2-(4-methoxybenzyl)cyclohex-1-enecarboxylate contaminated with the triflate starting material after purification on a Teledyne-Isco Combiflash machine (12 g gold column, hexanes→15% EtOAc/hexanes, gradient). The estimated yield of the desired product, accounting for impurity based on 1H-NMR analysis, is approximately 135 mg (~75%).

Step 2. 2-(4-Methoxybenzyl)cyclohex-1-enecarboxylic acid

In accordance with the procedure of Example 4, step 2, ethyl 2-(4-methoxybenzyl)cyclohex-1-enecarboxylate (156 mg of the impure material from step 1, ~0.49 mmol) was converted into 98 mg (~81%) of 2-(4-methoxybenzyl)cyclohex-1-enecarboxylic acid after purification on a Teledyne-Isco Combiflash machine (12 g gold column, hexanes→35% EtOAc/hexanes, gradient).

Step 3. Methyl 4-((2-(4-methoxybenzyl)cyclohex-1-enecarboxamido)methyl)benzoate In accordance with the procedure of Example 3, step 2, 2-(4-methoxybenzyl)cyclohex-1-enecarboxylic acid (96.3 mg, 0.39 mmol) and methyl 4-(aminomethyl)benzoate hydrochloride (81.3 mg, 0.39 mmol) were converted into 153 mg (99%) of methyl 4-((2-(4-methoxybenzyl)cyclohex-1-enecarboxamido)methyl)benzoate.

Step 4. 4-((2-(4-Methoxybenzyl)cyclohex-1-enecarboxamido)methyl)benzoic acid In accordance with the procedure of Example 3, step 3, methyl 4-((2-(4-methoxybenzyl)cyclohex-1-enecarboxamido)methyl)benzoate (10.6 mg, 0.0269 mmol) was converted into 5.6 mg (55%) of the title compound.

Example 34

4-((2-(4-Methoxybenzyl)cyclohexanecarboxamido)methyl)benzoic acid (from high R$_f$ ester diastereomer)

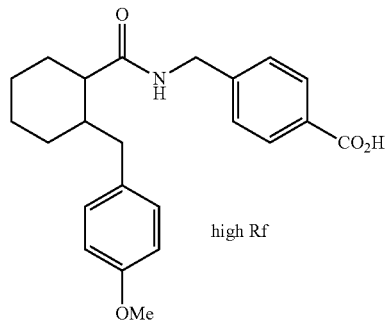 [SMILES: COc1ccc(CC2CCCCC2C(=O)NCc2ccc(C(=O)O)cc2)cc1]

high Rf

Step 1. Methyl 4-((2-(4-methoxybenzyl)cyclohexanecarboxamido)methyl)benzoate In accordance with the procedure of Example 5, step 1, methyl 4-((2-(4-methoxybenzyl)cyclohex-1-enecarboxamido)methyl)benzoate (40 mg, 0.10 mmol) was converted into 26.1 mg (65%) of methyl 4-((2-(4-methoxybenzyl)cyclohexanecarboxamido)methyl)benzoate (high R$_f$ diastereomer) and 10.1 mg (25%) of methyl 4-((2-(4-methoxybenzyl)cyclohexanecarboxamido)methyl)benzoate (low R$_f$ diastereomer).

Step 2. 4-((2-(4-Methoxybenzyl)cyclohexanecarboxamido)methyl)benzoic acid (from high R$_f$ ester diastereomer)

In accordance with the procedure of Example 3, step 3, methyl 4-((2-(4-methoxybenzyl)cyclohexanecarboxamido)methyl)benzoate (high R$_f$ diastereomer, 25.7 mg, 0.065 mmol) was converted into 15.9 mg (64%) of the title compound.

Example 35

4-((2-(4-Methoxybenzyl)cyclohexanecarboxamido)methyl)benzoic acid (from low R$_f$ ester diastereomer)

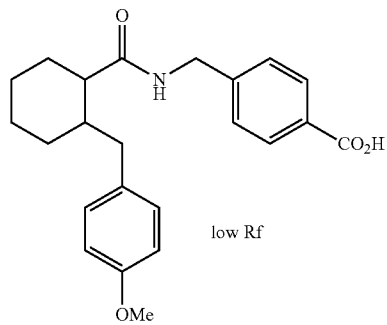 [SMILES: COc1ccc(CC2CCCCC2C(=O)NCc2ccc(C(=O)O)cc2)cc1]

low Rf

In accordance with the procedure of Example 3, step 3, methyl 4-((2-(4-methoxybenzyl)cyclohexanecarboxamido)methyl)benzoate (low R$_f$ diastereomer, 9.8 mg, 0.0248 mmol) was converted into 3.2 mg (34%) of the title compound.

Example 36

4-((3-(3,5-Dimethoxybenzyl)bicyclo[2.2.1]hept-2-ene-2-carboxamido)methyl)benzoic acid

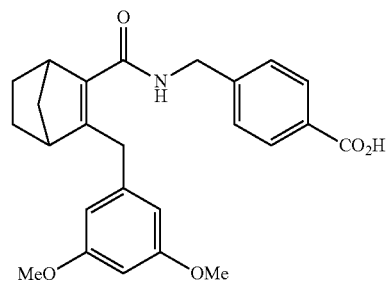 [SMILES: COc1cc(CC2=C(C(=O)NCc3ccc(C(=O)O)cc3)C3CCC2C3)cc(OC)c1]

Step 1. Methyl 3-oxobicyclo[2.2.1]heptane-2-carboxylate

A solution of lithium diisopropylamide (2.3 mL of a 2.0 M solution in THF, 4.6 mmol) was added to a −78° C. solution of norcamphor (Aldrich, 459 mg, 4.08 mmol) in THF (23.5 mL). After 15 min at −78° C., a solution of methyl cyanoformate (421 mg, 4.90 mmol) in THF (1 mL+1 mL rinse) was added. The mixture was allowed to warm to room temperature and stirred for 18 h. The reaction was quenched with saturated aqueous NH$_4$Cl and extracted with CH$_2$Cl$_2$ (3×). The combined extracts were dried (MgSO$_4$), filtered and concentrated. The resulting crude residue was purified on a Teledyne-Isco Combiflash machine (40 g gold column, 10% EtOAc/hexanes→30% EtOAc/hexanes, gradient), to afford 572 mg (83%) of methyl 3-oxobicyclo[2.2.1]heptane-2-carboxylate.

Step 2. Methyl 3-(((trifluoromethyl)sulfonyl)oxy)bicyclo[2.2.1]hept-2-ene-2-carboxylate In accordance with the procedure of Example 8, step 1, methyl 3-oxobicyclo[2.2.1]heptane-2-carboxylate (446 mg, 2.65 mmol) was converted into 316 mg (40%) of methyl 3-(((trifluoromethyl)sulfonyl)oxy)bicyclo[2.2.1]hept-2-ene-2-carboxylate.

Step 3. Methyl 3-(3,5-dimethoxybenzyl)bicyclo[2.2.1]hept-2-ene-2-carboxylate In accordance with the procedure of Example 8, step 2, methyl 3-(((trifluoromethyl)sulfonyl)oxy)bicyclo[2.2.1]hept-2-ene-2-carboxylate (160 mg, 0.533 mmol) and 3,5-dimethoxybenzylzinc(II) chloride (Aldrich, 1.3 mL of a 0.5 M solution in THF, 0.65 mmol) were converted after 3 days stirring at room temperature into 99 mg (61%) of methyl 3-(3,5-dimethoxybenzyl)bicyclo[2.2.1]hept-2-ene-2-carboxylate after purification on a Teledyne-Isco Combiflash machine (12 g gold column, hexanes→15% EtOAc/hexanes, gradient).

Step 4. 3-(3,5-Dimethoxybenzyl)bicyclo[2.2.1]hept-2-ene-2-carboxylic acid

In accordance with the procedure of Example 4, step 2, methyl 3-(3,5-dimethoxybenzyl)bicyclo[2.2.1]hept-2-ene-2-carboxylate (98 mg, 0.32 mmol) was converted into 31.4 mg (34%) of 3-(3,5-dimethoxybenzyl)bicyclo[2.2.1]hept-2-ene-2-carboxylic acid and 60.5 mg (65%) of (E)-3-(3,5-dimethoxybenzylidene)bicyclo[2.2.1]heptane-2-carboxylic acid (as a mixture of 2 stereoisomers) after purification on a Teledyne-Isco Combiflash machine (12 g gold column, hexanes→35% EtOAc/hexanes, gradient).

Step 5. Methyl 4-((3-(3,5-dimethoxybenzyl)bicyclo[2.2.1]hept-2-ene-2-carboxamido)methyl)benzoate In accordance with the procedure of Example 3, step 2, 3-(3,5-dimethoxybenzyl)bicyclo[2.2.1]-2-ene-2-carboxylic acid (31.4 mg, 0.109 mmol) and methyl 4-(aminomethyl)benzoate hydrochloride (22.8 mg, 0.11 mmol) were converted into 47 mg (quant.) of methyl 4-((3-(3,5-dimethoxybenzyl)bicyclo[2.2.1]hept-2-ene-2-carboxamido)methyl)benzoate.

Step 6. 4-((3-(3,5-Dimethoxybenzyl)bicyclo[2.2.1]hept-2-ene-2-carboxamido)methyl)benzoic acid In accordance with the procedure of Example 3, step 3, methyl 4-((3-(3,5-dimethoxybenzyl)bicyclo[2.2.1]hept-2-ene-2-carboxamido)methyl)benzoate (9.2 mg, 0.021 mmol) was converted into 4.0 mg (45%) of the title compound.

Example 37

4-(((1 S,2R,4R,E)-3-(3,5-Dimethoxybenzylidene)bicyclo[2.2.1]heptane-2-carboxamido)methyl)benzoic acid (racemic)

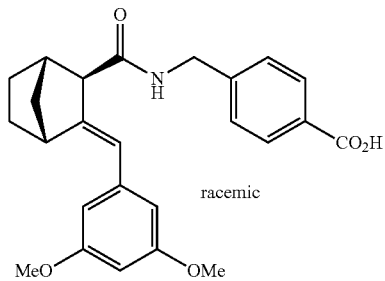 [SMILES: COc1cc(/C=C2\[C@@H]3CC[C@@H](C3)[C@H]2C(=O)NCc2ccc(C(=O)O)cc2)cc(OC)c1]

racemic

Step 1. (E)-Methyl 4-((3-(3,5-dimethoxybenzylidene)bicyclo[2.2.1]heptane-2-carboxamido)methyl)benzoate In accordance with the procedure of Example 3, step 2, (E)-3-(3,5-dimethoxybenzylidene)bicyclo[2.2.1]heptane-2-carboxylic acid (mixture of 2 stereoisomers, 60.5 mg, 0.210 mmol) and methyl 4-(aminomethyl)benzoate hydrochloride (43.6 mg, 0.210 mmol) were converted into 43.4 mg (48%) of racemic methyl 4-(((1S,2R,4R,E)-3-(3,5-dimethoxybenzylidene)bicyclo[2.2.1]heptane-2-carboxamido)methyl)benzoate and 23.3 mg (26%) of racemic methyl 4-(((1 S,2S,4R,E)-3-(3,5-dimethoxybenzylidene)bicyclo[2.2.1]heptane-2-carboxamido)methyl)benzoate.

Step 2. 4-(((1S,2R,4R,E)-3-(3,5-Dimethoxybenzylidene)bicyclo[2.2.1]heptane-2-carboxamido)methyl)benzoic acid (racemic)

In accordance with the procedure of Example 3, step 3, racemic methyl 4-(((1 S,2R,4R,E)-3-(3,5-dimethoxybenzylidene)bicyclo[2.2.1]heptane-2-carboxamido)methyl)benzoate (8.4 mg, 0.019 mmol) was converted into 3.1 mg (39%) of the title compound. Using the same conditions, racemic methyl 4-(((1S,2S,4R,E)-3-(3,5-dimethoxybenzylidene)bicyclo[2.2.1]heptane-2-carboxamido)methyl)benzoate (the other diastereomer from the previous step, 6.5 mg, 0.014 mmol) afforded 1.2 mg (19%) of the same title product.

Example 38

4-((3-(3,5-Dimethoxybenzyl)bicyclo[2.2.1]heptane-2-carboxamido)methyl)benzoic acid (from high $R_f$ ester diastereomer)

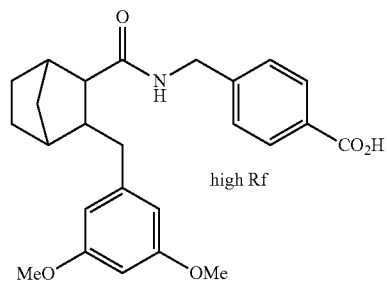 [SMILES: COc1cc(CC2C3CCC(C3)C2C(=O)NCc2ccc(C(=O)O)cc2)cc(OC)c1]

high Rf

Step 1. Methyl 4-((3-(3,5-dimethoxybenzyl)bicyclo[2.2.1]heptane-2-carboxamido)methyl)benzoate In accordance with the procedure of Example 5, step 1, methyl 4-((3-(3,5-dimethoxybenzyl)bicyclo[2.2.1]hept-2-ene-2-carboxamido)methyl)benzoate (40 mg, 0.092 mmol) was converted into 32 mg (80%) of methyl 4-((3-(3,5-dimethoxybenzyl)bicyclo[2.2.1]heptane-2-carboxamido)methyl)benzoate (high $R_f$ diastereomer, presumably 1 racemic cis isomer) and 3.8 mg (10%) of methyl 4-((3-(3,5-dimethoxybenzyl)bicyclo[2.2.1]heptane-2-carboxamido)methyl)benzoate (low $R_f$ diastereomer, mixture of 3 isomers, presumably the other racemic cis isomer and 2 trans isomers).

Step 2. 4-((2-(4-Methoxybenzyl)cyclohexanecarboxamido)methyl)benzoic acid (from high $R_f$ ester diastereomer)

In accordance with the procedure of Example 3, step 3, methyl 4-((3-(3,5-dimethoxybenzyl)bicyclo[2.2.1]heptane-2-carboxamido)methyl)benzoate (high $R_f$ diastereomer, 10.4 mg, 0.0238 mmol) was converted into 7.1 mg (70%) of the title compound.

Example 39

4-((3-(3,5-Dimethoxybenzyl)bicyclo[2.2.1]heptane-2-carboxamido)methyl)benzoic acid (from low $R_f$ ester diastereomer)

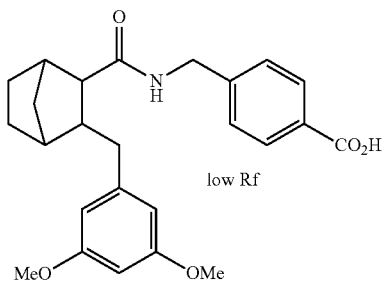 [SMILES: COc1cc(CC2C3CCC(C3)C2C(=O)NCc2ccc(C(=O)O)cc2)cc(OC)c1]

low Rf

In accordance with the procedure of Example 3, step 3, methyl 4-((3-(3,5-dimethoxybenzyl)bicyclo[2.2.1]heptane-2-carboxamido)methyl)benzoate (low $R_f$ diastereomer, mixture of 3 isomers, 3.8 mg, 0.0087 mmol) was converted into 1.4 mg (38%) of the title compound, still as a mixture of 3 isomers.

Biological Data

Binding Data

Data from running binding and activity studies on the compounds of the invention were carried out as described in U.S. Pat. No. 7,427,685, the contents of which are incorporated herein by reference.

$K_i$ Binding Data

Competition binding experiments were performed in a medium containing Hank's balanced salt solution, Hepes 20 mM, pH 7.3, membranes (~60 μg protein) or $2\times10^5$ cells from HEK 293 cells stably expressing human $EP_2$ receptors, [$^3$H]PGE2 (10 nM) and various concentrations of test compounds in a total volume of 300 μl. Reaction mixtures were incubated at 23° C. for 60 min, and were filtered over Whatman GF IB filters under vacuum. Filters were washed three times with 5 ml ice-cold buffer containing 50 mM Tris/HCl (PH 7.3). Non-specific binding was estimated in the presence of excess unlabeled PGE2 (10 μM). Binding data fitted to the binding model for a single class of binding sites, using nonlinear regression analysis. $IC_{50}$ values thus obtained were converted to $K_i$ using the equation of $K_i=(IC_{50}/(1+[L]/K_D)$ where [L] represents PGE2 concentration (10 nM) and $K_D$ the dissociation constant for [$^3$H]PGE2 at human $EP_2$ receptors (40 nM).

Radioligand Binding

Cells Stably Expressing $EP_1$, $EP_2$, $EP_4$, and FP Receptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; ION HCl is added to achieve a pH of 7.4).

The cell homogenate was centrifuged at 19000 rpm for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17-phenyl $PGF_{2\alpha}$ (5 nM) were performed in a 100 g 1 volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H-] $PGE_2$ (specific activity 180 Ci mmol) was used as the radio ligand for EP receptors. [$^3$H] 17-phenyl $PGF_{2\alpha}$ was employed for FP receptor binding studies. Binding studies employing $EP_1$, $EP_2$, $EP_4$ and FP receptors were performed in duplicate in at least three separate experiments. A 200 μl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]-$PGE_2$, or 5 nM [$^3$H] 17-phenyl $PGF_{2\alpha}$ and non-specific binding determined with $10^{-5}$ M of unlabeled $PGE_2$, or 17-phenyl $PGF_{2\alpha}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), were cultured in 100 mm culture dishes in high-glucose DMEM medium containing 10% fetal bovine serum, 2 mM I-glutamine, 250 μg/ml geneticin (G418) and 200 μg/ml hygromycin B as selection markers, and 100 units/ml penicillin G, 100 μg/ml streptomycin and 0.25 μg/ml amphotericin B.

(b) Calcium Signal Studies on the FLIPR™

Cells were seeded at a density of $5\times10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 μM, plates were washed four times with HBSS-HEPES buffer to remove excess dye leaving 100 μL in each well. Plates were re-equilibrated to 37° C. for a few minutes.

Cells were excited with an Argon laser at 488 nm, and emission was measured through a 510-570 nm bandwidth emission filter (FLIPR™, Molecular Devices, Sunnyvale, Calif.). Drug solution was added in a 50 μL volume to each well to give the desired final concentration. The peak increase in fluorescence intensity was recorded for each well. On each plate, four wells each served as negative (HBSS-HEPES buffer) and positive controls (standard agonists: BW245C (hDP); $PGE_2(hEP_1$; $hEP_2$/Gqs5; $hEP_{3A}$/Gqi5; $hEP_4$/Gqs5); $PGF_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$. The duplicate values were averaged. In either, HTS or CoRe format each compound was tested on at least 3 separate plates using cells from different passages to give an n≥3.

cAMP Assay

A 384-well drug plate was prepared to contain 6 test compounds, PGE$_2$ and cAMP in 16 serial dilutions in triplicate, using a Biomek station. HEK-EBNA cells expressing a target PG receptor subtype (EP$_2$ or EP$_4$) were suspended in a stimulation buffer (HBSS, 0.1% BSA, 0.5 mM IBMX and 5 mM HEPES, pH 7.4) in a density of $10^4$ cells/5 μL. The reaction was initiated by mixing 5 μL drug dilutions with 5 μL of HEK-EBNA cells in a well, carried out for 30 min at room temperature, and followed by the addition of 5 μL anti-cAMP acceptor beads in the control buffer with Tween-20 (25 mM NaCl, 0.03% Tween-20, 5 mM HEPES, pH 7.4). After 30 min in the dark at room temperature, the mixtures were incubated with 15 μL biotinylated-cAMP/strepavidin donor beads in Lysis/Detection buffer (0.1% BSA, 0.3% Tween-20 and 5 mM HEPES, pH 7.4) for 45 min at the room temperature. Fluorescence changes were read using a Fusion-alpha HT microplate reader.

The results set forth below in Table 1 demonstrate that the compounds disclosed herein are selective prostaglandin EP$_4$ agonists and antagonists, and are thus useful for the treatment of pathological conditions associated with EP$_4$ receptors. In Table 1, "NA" indicates no activity.

TABLE 1

| Ex. | Structure | EP2 Data | | EP4 data | | Other Receptors (EC50 in nM) | | | | | |
|---|---|---|---|---|---|---|---|---|---|---|---|
| | | cAMP EC50 | Ki | cAMP EC50 | KI | hFP | hEP1 | hEP3A | hTP | hIP | hDP |
| 1 | 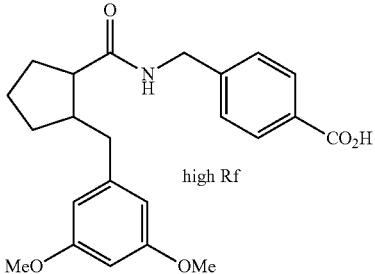 [SMILES: COc1cc(CC2CCCC2C(=O)NCc2ccc(C(=O)O)cc2)cc(OC)c1] high Rf | 6186 | | weak agonist | 30 | NA | NA | NA | NA | NA | NA |
| 2 | 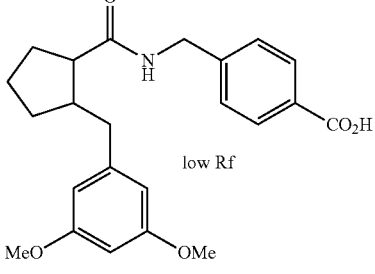 low Rf | >10000 | 9 | 84 | | NA | NA | NA | NA | NA | NA |
| 3 | 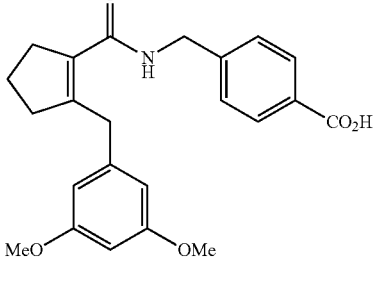 | 33 | 1124 | 1 | 5 | NA | NA | NA | NA | NA | NA |
| 4 | 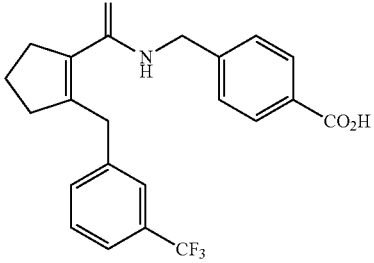 | 2 | 109 | >10000 | 7 | NA | NA | NA | NA | NA | NA |

TABLE 1-continued
| Ex. | Structure | EP2 Data cAMP EC50 | Ki | EP4 data cAMP EC50 | KI | Other Receptors (EC50 in nM) hFP | hEP1 | hEP3A | hTP | hIP | hDP |
|---|---|---|---|---|---|---|---|---|---|---|---|
| 5 | 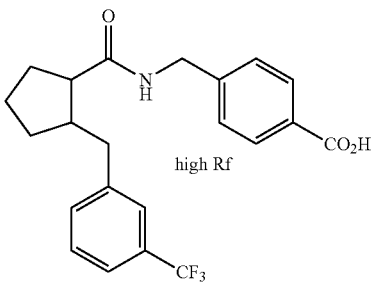 [SMILES: O=C(O)c1ccc(CNC(=O)C2CCCC2Cc2cccc(C(F)(F)F)c2)cc1] high Rf | 13 | 154 | >10000 | 8 | NA | NA | NA | NA | NA | NA |
| 6 | 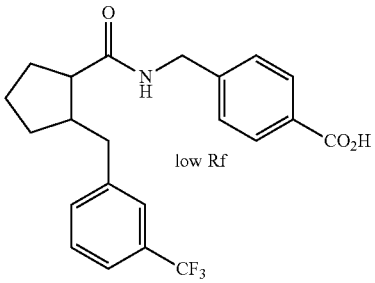 [SMILES: O=C(O)c1ccc(CNC(=O)C2CCCC2Cc2cccc(C(F)(F)F)c2)cc1] low Rf | 10 | 733 | >10000 | 18 | NA | NA | NA | NA | >10000 | NA |
| 7 | 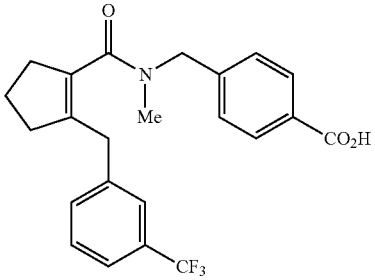 [SMILES: CN(Cc1ccc(C(=O)O)cc1)C(=O)C1=C(Cc2cccc(C(F)(F)F)c2)CCC1] | | | | 1570 | | | | | | |
| 8 | 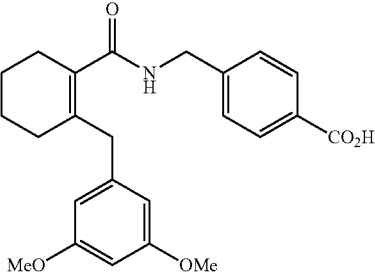 [SMILES: COc1cc(CC2=C(C(=O)NCc3ccc(C(=O)O)cc3)CCCC2)cc(OC)c1] | 2 | 177 | 0.2 | 1 | NA | NA | NA | NA | NA | NA |
| 9 | 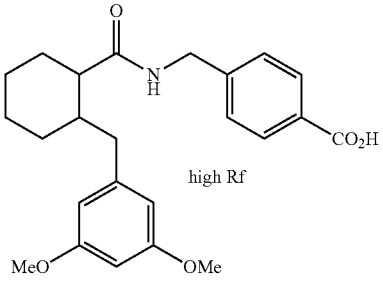 [SMILES: COc1cc(CC2CCCCC2C(=O)NCc2ccc(C(=O)O)cc2)cc(OC)c1] high Rf | 389 | 2148 | >10000 | 2 | NA | NA | NA | NA | NA | NA |

TABLE 1-continued
| Ex. | Structure | EP2 Data | | EP4 data | | Other Receptors (EC50 in nM) | | | | | |
| --- | --- | --- | --- | --- | --- | --- | --- | --- | --- | --- | --- |
| | | cAMP EC50 | Ki | cAMP EC50 | KI | hFP | hEP1 | hEP3A | hTP | hIP | hDP |
| 10 | 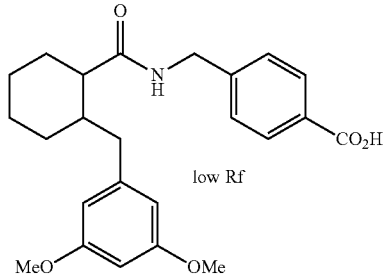 [SMILES: COc1cc(CC2CCCCC2C(=O)NCc2ccc(C(=O)O)cc2)cc(OC)c1] low Rf | 25 | 908 | 0.2 | 2 | NA | NA | NA | NA | NA | NA |
| 11 | 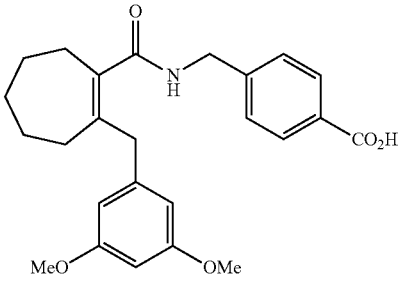 [SMILES: COc1cc(CC2=C(C(=O)NCc3ccc(C(=O)O)cc3)CCCCC2)cc(OC)c1] | 48 | 2776 | >10000 | 1 | NA | NA | NA | NA | >10000 | NA |
| 12 | 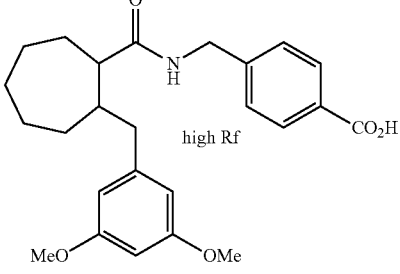 high Rf | 1308 | >10000 | >10000 | 9 | NA | NA | NA | NA | NA | NA |
| 13 | 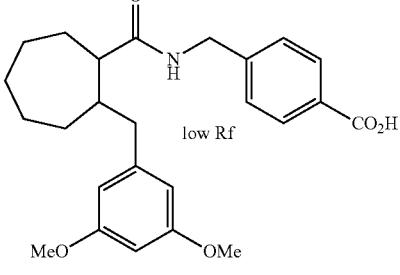 low Rf | 573 | 6297 | 0.2 | 2 | NA | NA | NA | NA | NA | NA |
| 14 | 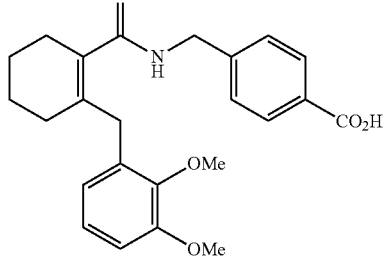 | | | 1194 | >10000 | 45 | NA | NA | NA | NA | NA |

TABLE 1-continued
| Ex. | Structure | EP2 Data | | EP4 data | | Other Receptors (EC50 in nM) | | | | | |
|---|---|---|---|---|---|---|---|---|---|---|---|
| | | cAMP EC50 | Ki | cAMP EC50 | KI | hFP | hEP1 | hEP3A | hTP | hIP | hDP |
| 15 | 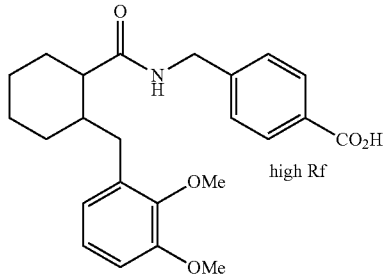 [SMILES: COc1cccc(CC2CCCCC2C(=O)NCc2ccc(C(=O)O)cc2)c1OC] high Rf | | 7481 | >10000 | 17 | NA | NA | NA | NA | NA | NA |
| 16 | 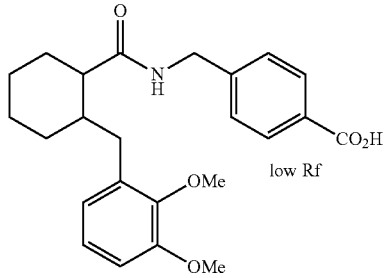 [SMILES: COc1cccc(CC2CCCCC2C(=O)NCc2ccc(C(=O)O)cc2)c1OC] low Rf | | 4119 | >10000 | 114 | NA | NA | NA | NA | NA | NA |
| 17 | 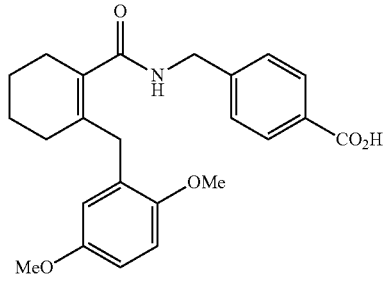 [SMILES: COc1ccc(OC)c(CC2=C(C(=O)NCc3ccc(C(=O)O)cc3)CCCC2)c1] | | 403 | >10000 | 8 | NA | NA | NA | NA | NA | NA |
| 18 | 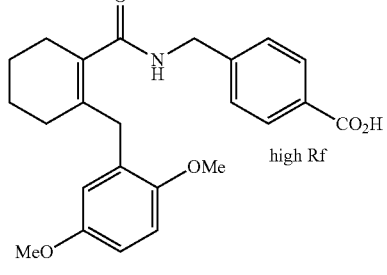 high Rf | | 462 | >10000 | 16 | NA | NA | NA | NA | NA | NA |
| 19 | 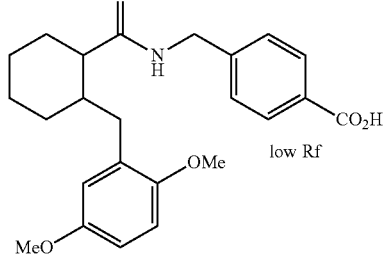 low Rf | | 393 | 0.2 | 2 | NA | NA | NA | NA | NA | NA |

TABLE 1-continued

| Ex. | Structure | EP2 Data | | EP4 data | | Other Receptors (EC50 in nM) | | | | | |
|---|---|---|---|---|---|---|---|---|---|---|---|
| | | cAMP EC50 | Ki | cAMP EC50 | KI | hFP | hEP1 | hEP3A | hTP | hIP | hDP |
| 20 | [structure: cyclooctene with carboxamide-CH2-C6H4-CO2H, and CH2-(3,5-dimethoxyphenyl)] | | | >10000 | >10000 0.2 | NA | NA | NA | NA | NA | NA |
| 21 | [structure: cyclohexene carboxamide benzyl-CO2H, 3,4-dimethoxybenzyl] | | | >10000 | 4 | | | | | | |
| 22 | [structure: cyclohexane carboxamide benzyl-CO2H, 3,4-dimethoxybenzyl] high Rf | | | >10000 | 4 | | | | | | |
| 23 | [structure: cyclohexane carboxamide benzyl-CO2H, 3,4-dimethoxybenzyl] low Rf | | | >10000 | 8 | | | | | | |
| 24 | [structure: cyclohexene carboxamide benzyl-CO2H, 2-chlorobenzyl] | | | 83 | >10000 4 | NA | NA | NA | NA | NA | NA |

TABLE 1-continued
| | | EP2 Data | | EP4 data | | Other Receptors (EC50 in nM) | | | | | |
|---|---|---|---|---|---|---|---|---|---|---|---|
| Ex. | Structure | cAMP EC50 | Ki | cAMP EC50 | KI | hFP | hEP1 | hEP3A | hTP | hIP | hDP |
| 25 | 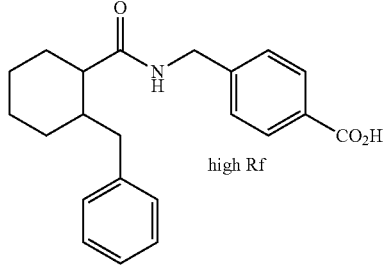 [SMILES: O=C(O)c1ccc(CNC(=O)C2CCCCC2Cc2ccccc2)cc1] high Rf | 4947 | >10000 | 58 | | NA | NA | NA | NA | NA | NA |
| 26 | 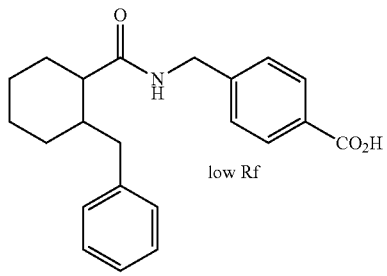 [SMILES: O=C(O)c1ccc(CNC(=O)C2CCCCC2Cc2ccccc2)cc1] low Rf | 2923 | 35 | 116 | | NA | NA | NA | NA | NA | NA |
| 27 | 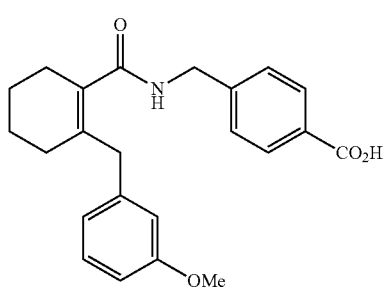 [SMILES: COc1cccc(CC2=C(C(=O)NCc3ccc(C(=O)O)cc3)CCCC2)c1] | 138 | >10000 | 2 | | NA | NA | NA | NA | NA | NA |
| 28 | 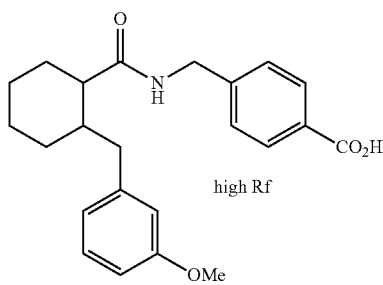 [SMILES: COc1cccc(CC2CCCCC2C(=O)NCc2ccc(C(=O)O)cc2)c1] high Rf | 2351 | >10000 | 4 | | NA | NA | NA | NA | NA | NA |
| 29 | 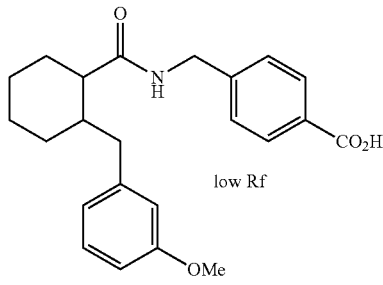 [SMILES: COc1cccc(CC2CCCCC2C(=O)NCc2ccc(C(=O)O)cc2)c1] low Rf | 2574 | 4 | 19 | | NA | NA | NA | NA | NA | NA |

TABLE 1-continued

| | | EP2 Data | | EP4 data | | Other Receptors (EC50 in nM) | | | | | |
|---|---|---|---|---|---|---|---|---|---|---|---|
| Ex. | Structure | cAMP EC50 | Ki | cAMP EC50 | KI | hFP | hEP1 | hEP3A | hTP | hIP | hDP |
| 30 | (structure with OMe, cyclohexene, amide, benzoic acid) | | | 219 | >10000 | 6 | | | | | |
| 31 | (structure with OMe, cyclohexane, amide, benzoic acid, high Rf) | | | 994 | >10000 | 5 | | | | | |
| 32 | (structure with OMe, cyclohexane, amide, benzoic acid, low Rf) | | | 1319 | >10000 | 7 | | | | | |
| 33 | (structure with cyclohexene, amide, benzoic acid, OMe para) | | | 1142 | >10000 | 1 | | | | | |
| 34 | (structure with cyclohexane, amide, benzoic acid, OMe para, high Rf) | | | >10000 | >10000 | 44 | | | | | |

TABLE 1-continued
| Ex. | Structure | EP2 Data cAMP EC50 | Ki | EP4 data cAMP EC50 | KI | Other Receptors (EC50 in nM) hFP | hEP1 | hEP3A | hTP | hIP | hDP |
|---|---|---|---|---|---|---|---|---|---|---|---|
| 35 | 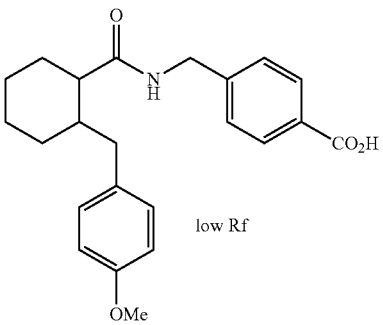 [SMILES: COc1ccc(CC2CCCCC2C(=O)NCc2ccc(C(=O)O)cc2)cc1] low Rf | | | >10000 | >10000 | 86 | | | | | |
| 36 | 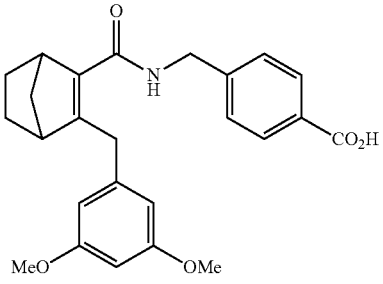 [SMILES: COc1cc(CC2=C(C(=O)NCc3ccc(C(=O)O)cc3)C3CCC2C3)cc(OC)c1] | | | | 1008 | | | | | | |
| 37 | 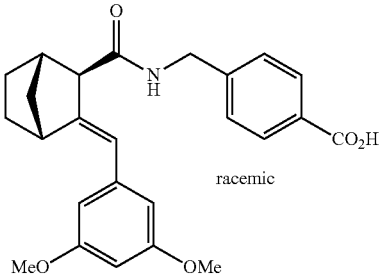 [SMILES: COc1cc(/C=C2\[C@@H]3CC[C@@H](C3)[C@H]2C(=O)NCc2ccc(C(=O)O)cc2)cc(OC)c1] racemic | | | NA | >10000 | 323 | | | | | |
| 38 | 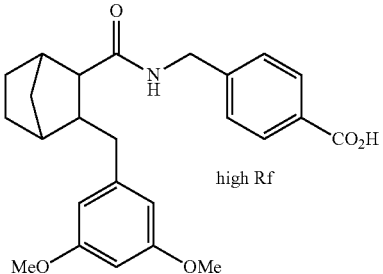 [SMILES: COc1cc(CC2C3CCC(C3)C2C(=O)NCc2ccc(C(=O)O)cc2)cc(OC)c1] high Rf | | | NA | >10000 | 402 | | | | | |
| 39 | 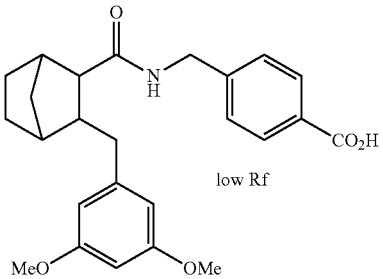 [SMILES: COc1cc(CC2C3CCC(C3)C2C(=O)NCc2ccc(C(=O)O)cc2)cc(OC)c1] low Rf | | | NA | >10000 | 77 | | | | | |

Formulations and Compositions

Those skilled in the art will readily understand that for administration or the manufacture of medicaments the compounds disclosed herein can be admixed with pharmaceutically acceptable excipients which per se are known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and U.S. Pat. No. 4,265,874 to form osmotic therapeutic tablets for control release, which are herein incorporated by reference in their entireties. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the compounds can be in the range of about 0.5 or about 1 to about 100 mg/kg/day.

In some embodiments, the amount of the active compound in a pharmaceutical composition is 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 3.0%, 4.0% and 5.0% w/w.

In some embodiments, an effective amount, e.g., a therapeutically effective amount, of the active compound in a pharmaceutical composition is afforded at a concentration of about $1 \times 10^{-7}$ to 50% (w/w), about 0.001 to 50% (w/w), about 0.01 to 50% (w/w), about 0.1 to 50% (w/w), or about 1 to 50% (w/w). In some embodiments, the therapeutically effective amount of the active compound in a pharmaceutical composition is 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9% and 1.0%, 1.1%, 1.2%, 1.3%, 1.4%, 1.5%, 1.6%, 1.7%, 1.8%, 1.9%, 2.0%, 3.0%, 4.0% and 5.0% w/w.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions can be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methylcellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |

-continued

| Ingredient | Amount (% w/v) |
|---|---|
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The compositions may be administered between 1 and 7 days a week, for a period of time necessary to achieve the desired results, which may be several days to several months. The compositions can be administered once or several times (2, 3, 4, or more times) a day depending on the desired effect. In certain embodiments, the compositions can be administered every 1, 2, 3, 4, 5, 6, or 7 days. In another embodiment, the compositions can be administered one or more times every 1, 2, 3, or 4 weeks. The administration can be on a monthly or bi-monthly basis. Further, the compositions can be administered for 1, 2, 3, 6, 9, or 12 months or more. In certain embodiments, the compositions can be administered on an ongoing basis to maintain a desired result.

The disclosed compounds can be administered as part of a composition. As used herein, "formulation" and "composition" may be used interchangeably and refer to a combination of elements that is presented together for a given purpose. Such terms are well known to those of ordinary skill in the art.

As used herein, "carrier," "inert carrier," and "acceptable carrier" may be used interchangeably and refer to a carrier which may be combined with the presently disclosed compounds in order to provide a desired composition. Those of ordinary skill in the art will recognize a number of carriers that are well known for making specific pharmaceutical and/or cosmetic compositions. Desirably, the carrier is suitable for application to keratinous surfaces or other areas of the body. Upon application, acceptable carriers are substantially free of adverse reactions with skin and other keratinous surfaces. For example, the carriers may take the form of fatty or non-fatty creams, milky suspensions or emulsion-in-oil or oil-in-water types, lotions, gels or jellies, colloidal or non-colloidal aqueous or oily solutions, pastes, aerosols, soluble tablets or sticks. In accordance with one embodiment, the composition includes a dermatologically compatible vehicle or carrier. The vehicle which may be employed for preparing compositions may comprise, for example, aqueous solutions such as e.g., physiological salines, oil solutions or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity.

Examples of additional agents which can be included in the present compositions are anti-itch, anti-cellulite, anti-scarring, and anti-inflammatory agents, anesthetics, anti-irritants, vasoconstrictors, vasodilators, as well as agents to prevent/stop bleeding, and improve/remove pigmentation, moisturizers, desquamating agents, tensioning agents, anti-acne agents. Anti-itch agents can include methyl sulphonyl methane, sodium bicarbonate, calamine, allantoin, kaolin, peppermint, tea tree oil and combinations thereof. Anti-cellulite agents can include forskolin, xanthine compounds such as, but not limited to, caffeine, theophylline, theobromine, and aminophylline, and combinations thereof. Anesthetic agents can include lidocaine, benzocaine, butamben, dibucaine, oxybuprocaine, pramoxine, proparacaine, proxymetacaine, tetracaine, and combinations thereof. Anti-scarring agents can include IFN-.gamma., fluorouracil, poly (lactic-co-glycolic acid), methylated polyethylene glycol, polylactic acid, polyethylene glycol and combinations thereof. Anti-inflammatory agents can include dexamethasone, prednisolone, corticosterone, budesonide, estrogen, sulfasalazine, mesalamine and derivatives and combinations thereof. Additionally, active agents such as epinephrine, thymidine, cytidine, uridine, antiypyrin, aminocaproic acid, tranexamic acid, eucalyptol, allantoin, glycerin, and sodium selenite, can be included. Formulations can further comprise degradation inhibitors. Degradation inhibitors, include but are not limited to, glycosaminoglycans (e.g., heparin, heparin sulfate, dermatan sulfate, chrondroitin sulfate, o-sulfated HA, lnamarin, and amygdalin), antioxidants (e.g. ascorbic acid, melatonin, vitamin C, vitamin E), proteins (e.g., serum hyaluronidase inhibitor), and fatty acids (e.g. saturated $C_{10}$ to $C_{22}$ fatty acids). In certain embodiments, additional active agent is an antioxidant. In certain embodiments, the antioxidant comprises a vitamin C and/or a vitamin E such as d-alpha-tocopheryl polyethylene glycol 1000 succinate (TPGS).

The disclosed compositions are well suited for topical, subcutaneous, intradermal, subdermal, subcutaneous, and transdermal administration. Topical administration relates to the use of a composition applied to the surface of the skin at the site of a skin blemish for exertion of local action. Accordingly, such topical compositions include those pharmaceutical or cosmetic forms in which the composition is applied externally by direct contact with the skin surface to be treated, such as the face, neck, arms, legs, and/or torso. Conventional pharmaceutical or cosmetic forms for this purpose include ointments, liniments, creams, shampoos, lotions, pastes, jellies, sprays, aerosols, and the like, and may further be applied directly or in patches or impregnated dressings depending on blemish and skin region to be treated. The term "ointment" embraces formulations (including creams) having oleaginous, water-soluble and emulsion-type bases, e.g., petrolatum, lanolin, polyethylene glycols, as well as mixtures of these.

The compositions are appropriate for mesotherapy applications as well. Mesotherapy is a non-surgical cosmetic treatment technique involving intra-epidermal, intra-dermal, and/or subcutaneous injection of a composition. The compositions are administered in the form of small multiple droplets into the epidermis, dermo-epidermal junction, and/or the dermis.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metipranolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and α₂-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists and other neuroprotective agents such as Ca²⁺ channel blockers such as memantine, amantadine, rimantadine, nitroglycerin, dextrophan, dextromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, bamidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chloprostenol, fluprostenol, 13,14-dihydro-chloprostenol, isopropyl unoprostone, latanoprost and the like.

Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

Pathological conditions associated with EP4 receptors include, but are not limited to, acute hepatitis, asthma, bronchitis, burn, chronic obstructive respiratory diseases, Crohn's disease, digestive ulcer, glaucoma (and other diseases related to elevated intraocular pressure), hemophagous syndrome, hepatopathy, hypercytokinemia at dialysis, hypertension, immunological diseases (autoimmune diseases, organ transplantation, etc.), inflammation (such as rheumatoid arthritis), Kawasaki disease, liver injury, macrophage activation syndrome, myocardial ischemia, nephritis, nerve cell death, osteoporosis and diseases associated with bone disorders, premature birth, pulmonary emphysema, pulmonary fibrosis, pulmonary injury, renal failure, sepsis, sexual dysfunction, shock, sleep disorder, Still disease, stomatitis, systemic granuloma, systemic inflammatory syndrome, thrombosis and stroke, and ulcerative colitis.

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated.

The foregoing descriptions details specific methods and compositions that can be employed to practice the present invention, and represents the best mode contemplated. It should not be construed as limiting the overall scope hereof; rather, the ambit of the present invention is to be governed only by the lawful construction of the appended claims.

What is claimed:

1. A compound having the following structure:

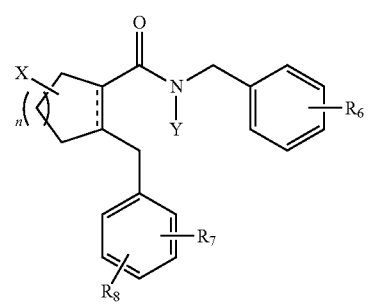

or a pharmaceutically acceptable salt or diastereomer or enantiomer thereof, wherein:

the dashed line is a single or a double bond;

Y is H or $CH_3$;

X is zero, one or two substituents on the cycloalkane or cycloalkene ring, said substituents chosen from the group consisting of $C_1$-$C_6$ alkyl, hydroxyalkyl, aryl, halogen, cycloalkene, $CF_3$, $C(O)R$, $COCF_3$, $SO_2N(R)_2$, $SO_2NH_2$, $NO_2$, and CN;

n is selected from the group consisting of 0, 1, 2, 3, or 4;

R is $C_1$-$C_6$ alkyl;

$R_6$ is $CO_2H$, $CH_3$, $CO_2R_2$, $CH_2OR_2$, $CONR_2R_3$ or tetrazol-5-yl;

$R_7$ is selected from the group consisting of H, $CF_3$, $OCH_3$; and $R_8$ is selected form the group consisting of H and $OCH_3$.

2. The compound of claim 1, wherein $R_6$ is $CO_2H$ and n is selected from the group consisting of 0, 1 and 2.

3. The compound of claim 1, wherein n is selected from the group consisting of 0, 1 and 2 and the dashed line represents a double bond.

4. The compound of claim 3, wherein $R_7$ and $R_8$ are $OCH_3$.

5. The compound of claim 3, wherein $R_7$ is $CF_3$ and $R_8$ is H.

6. The compound of claim 1 wherein n is selected from the group consisting of 1 and 2.

7. The compound of claim 1 wherein the dashed line represents a single bond.

8. The compound of claim 1 wherein n is selected from the group consisting of 3 and 4.

9. The compound of claim 1 wherein $R_7$ and $R_8$ are $OCH_3$.

10. The compound of claim 1 selected from the group consisting of:

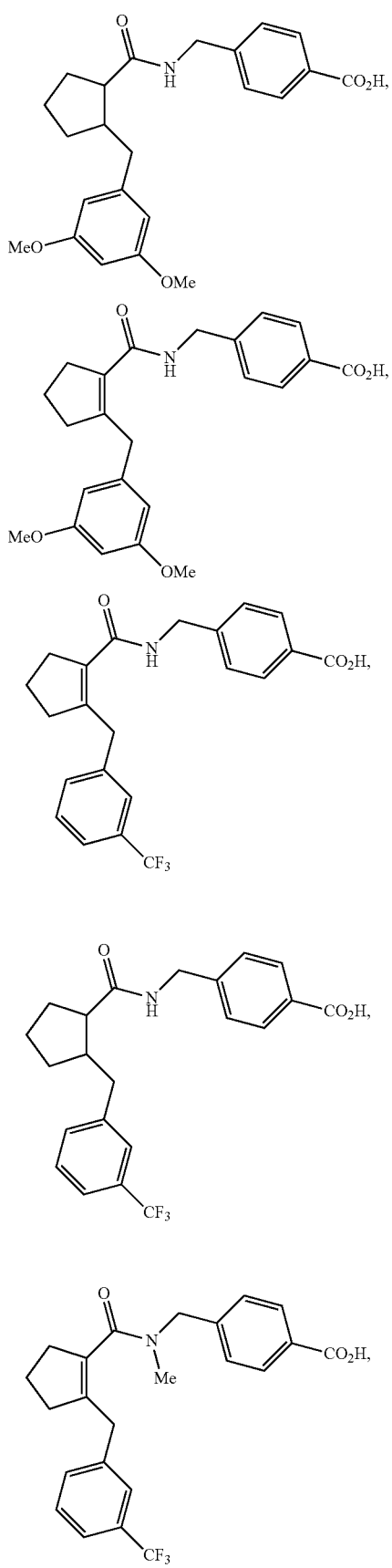
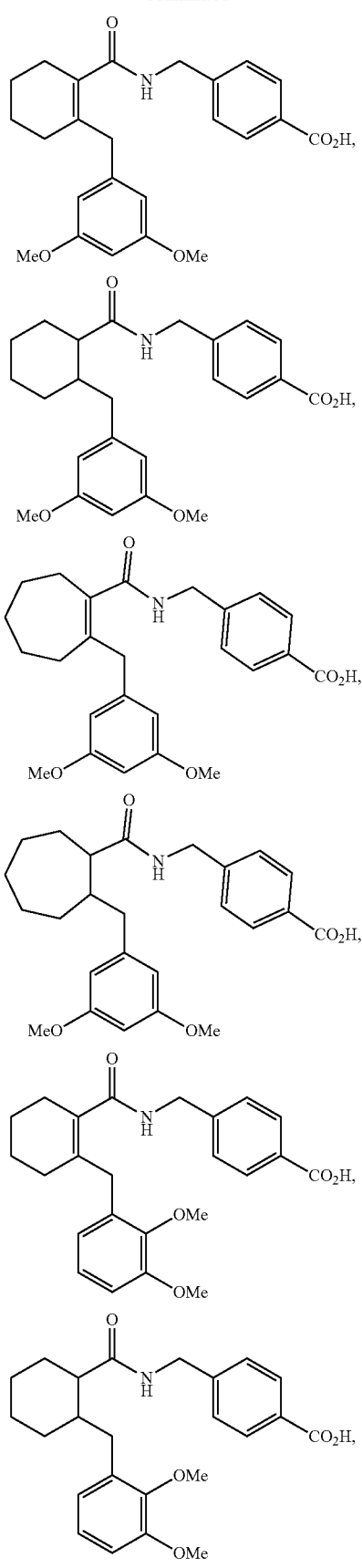

-continued
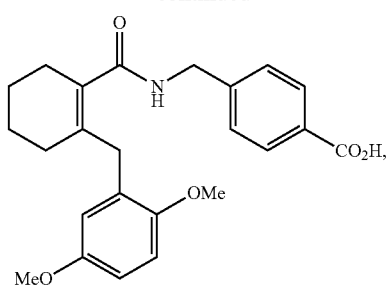
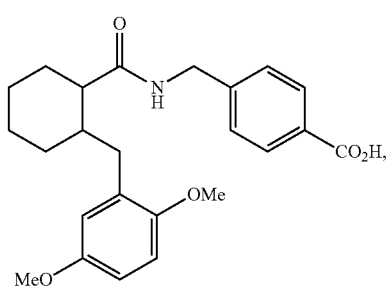
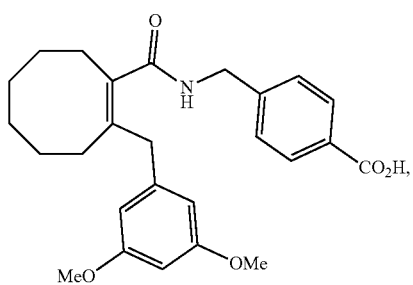
-continued
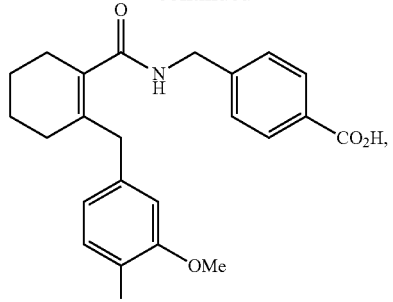
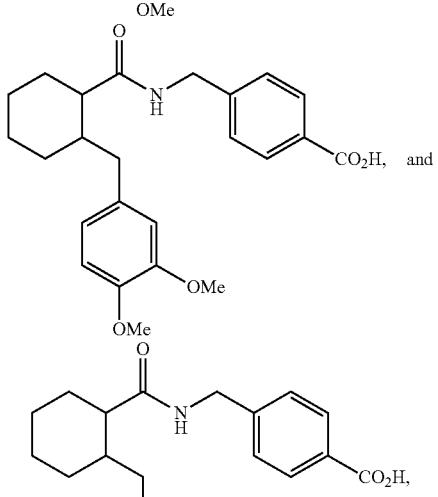
and pharmaceutically acceptable salts, diastereomers, and enantiomers thereof.
11. A pharmaceutical composition comprising a compound of claim 1 and a pharmaceutically acceptable carrier.
12. A method of treating glaucoma, the method comprising administering an effective amount of the compound of claim 1 to an individual in need thereof.
* * * * *

UNITED STATES PATENT AND TRADEMARK OFFICE
CERTIFICATE OF CORRECTION

PATENT NO. : 9,926,262 B2
APPLICATION NO. : 15/316786
DATED : March 27, 2018
INVENTOR(S) : David W. Old et al.

Page 1 of 4

It is certified that error appears in the above-identified patent and that said Letters Patent is hereby corrected as shown below:

In the Specification

In Column 1, Line 7, delete "371" and insert -- 35 --, therefor.

In Column 1, Line 30, delete "monophsophate" and insert -- monophosphate --, therefor.

In Column 2, Line 35, after "4" insert -- ; --.

In Column 2, Line 36, after "1" insert -- ; --.

In Column 2, Line 44, delete "form" and insert -- from --, therefor.

In Column 3, Line 14, delete "form" and insert -- from --, therefor.

In Column 3, Line 62, delete "form" and insert -- from --, therefor.

In Column 4, Line 3, delete "form" and insert -- from --, therefor.

In Column 4, Lines 6-19, delete " 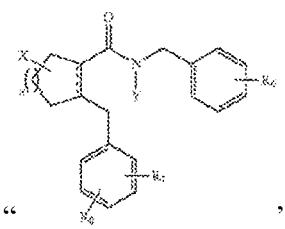 " and

Signed and Sealed this
Twenty-second Day of May, 2018

Andrei Iancu
*Director of the United States Patent and Trademark Office* insert -- 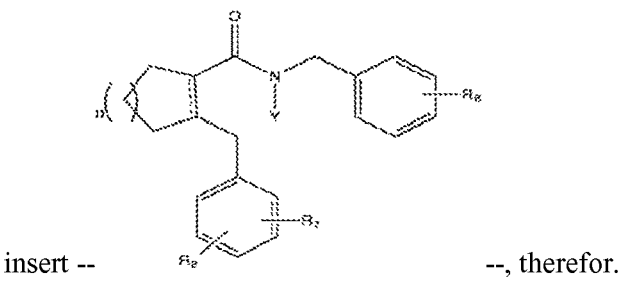 --, therefor.

In Column 4, Line 27, delete "form" and insert -- from --, therefor.

In Column 4, Line 35, delete "form" and insert -- from --, therefor.

In Column 4, Line 65, delete "form" and insert -- from --, therefor.

In Column 5, Line 15, delete "form" and insert -- from --, therefor.

In Column 7, Line 32, delete "enentiomer" and insert -- enantiomer --, therefor.

In Column 7, Line 46, delete "form" and insert -- from --, therefor.

In Column 7, Line 55, delete "form" and insert -- from --, therefor.

In Column 8, Line 3, after "wherein" delete "and".

In Column 13, Line 9, delete "form" and insert -- from --, therefor.

In Column 13, Line 34, after "wherein" delete "and".

In Column 19, Line 28, delete "galactunoric" and insert -- galacturonic --, therefor.

In Column 19, Line 62, delete "and or" and insert -- and/or --, therefor.

In Column 22, Lines 45-50, delete " 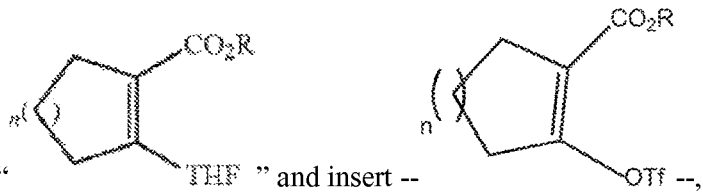 " and insert -- --, therefor.

In Column 28, Line 42, delete ") methyl)" and insert -- )methyl) --, therefor.

In Column 28, Line 45, delete "hexafluorborate" and insert -- hexafluoroborate --, therefor.

In Column 29, Line 34, delete "3-trifluormethylbenzylzinc" and insert -- 3-trifluoromethylbenzylzinc --, therefor.

CERTIFICATE OF CORRECTION (continued)
U.S. Pat. No. 9,926,262 B2

In Column 29, Line 63, delete ") methyl)" and insert -- )methyl) --, therefor.

In Column 30, Line 55, delete ") methyl)" and insert -- )methyl) --, therefor.

In Column 32, Line 37, delete "0 OC" and insert -- 0° C. --, therefor.

In Column 36, Line 26, delete ") methyl)" and insert -- )methyl) --, therefor.

In Column 39, Line 53, delete ") methyl)" and insert -- )methyl) --, therefor.

In Column 53, Line 35, delete "4-(((1 S," and insert -- 4-(((1S, --, therefor.

In Column 54, Line 7, delete "4-(((1 S," and insert -- 4-(((1S, --, therefor.

In Column 55, Line 50, delete "(IC$_{50}$/(1+[L]/K$_D$)" and insert -- IC$_{50}$/(1+[L]/K$_D$) --, therefor.

In Column 55, Line 67, delete "[$^3$H-]" and insert -- [$^3$H] --, therefor.

In Column 56, Line 1, delete "100 g 1" and insert -- 100 μl --, therefor.

In Column 56, Line 8, delete "[$^3$H-]" and insert -- [$^3$H] --, therefor.

In Column 58, Line 4, delete "/strepavidin" and insert -- /streptavidin --, therefor.

In Columns 63-64, Line 7 (TABLE 1-continued), delete " 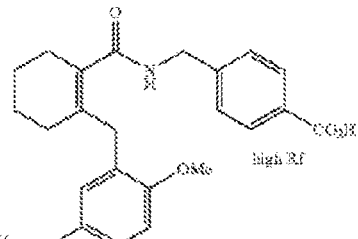 " and insert -- 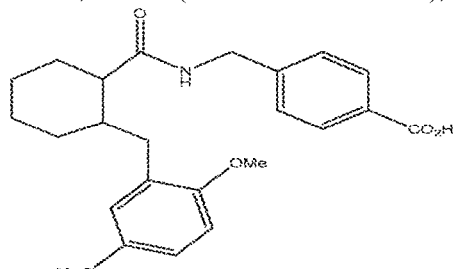 --, therefor.

In Column 73, Line 19, delete "distcarate" and insert -- distearate --, therefor.

In Column 76, Line 18, delete "antiypyrin," and insert -- antiypyrine, --, therefor.

In Column 76, Line 23, delete "chrondroitin" and insert -- chondroitin --, therefor.

CERTIFICATE OF CORRECTION (continued)
U.S. Pat. No. 9,926,262 B2

In Column 76, Line 24, delete "Inamarin," and insert -- linamarin, --, therefor.

In Column 76, Line 67, delete "metiparanolol," and insert -- metipranolol, --, therefor.

In Column 77, Line 7, after "thereof;" delete "and".

In Column 77, Line 18, delete "pilocarbine" and insert -- pilocarpine --, therefor.

In Column 77, Line 20, delete "chlolinesterase" and insert -- Cholinesterase --, therefor.

In Column 77, Line 25, delete "dextrophan," and insert -- dextrorphan, --, therefor.

In Column 77, Line 31, delete "nifedimpine," and insert -- nifedipine, --, therefor.

In Column 77, Line 31, delete "bamidipine," and insert -- barnidipine, --, therefor.

In Column 77, Lines 38-39, delete "chloprostenol," and insert -- cloprostenol, --, therefor.

In Column 77, Line 39, delete "-chloprostenol," and insert -- -cloprostenol, --, therefor.

In the Claims

In Column 78, Line 46, in Claim 1, delete "form" and insert -- from --, therefor.